United States Patent
Adang et al.

(10) Patent No.: US 6,432,921 B2
(45) Date of Patent: Aug. 13, 2002

(54) THROMBIN INHIBITORS

(75) Inventors: A. E. P. Adang, Eindhoven; C. A. A. van Boeckel, Oss; J. A. M. Peters, Oss; P. D. J. Grootenhuis, Oss, all of (NL)

(73) Assignee: Akzo Nobel N.V. (NL)

( * ) Notice: Subject to any disclaimer, the term of this patent is extended or adjusted under 35 U.S.C. 154(b) by 146 days.

(21) Appl. No.: 09/068,074

(22) PCT Filed: Oct. 30, 1996

(86) PCT No.: PCT/EP96/04785

§ 371 (c)(1),
(2), (4) Date: May 1, 1998

(87) PCT Pub. No.: WO97/17363

PCT Pub. Date: May 15, 1997

(30) Foreign Application Priority Data

Nov. 3, 1995 (EP) .............................................. 95202982
Dec. 19, 1995 (EP) .............................................. 95203554

(51) Int. Cl.[7] ........................ A61K 38/06; A61K 38/07
(52) U.S. Cl. ........................ 514/18; 530/330; 530/331
(58) Field of Search ................................ 530/330, 331; 514/18

(56) References Cited

U.S. PATENT DOCUMENTS 5,523,308 A    6/1996 Constanzo et al. ......... 514/317

FOREIGN PATENT DOCUMENTS

| WO | 96/19483 | 6/1996 |
| WO | 96/40741 | 12/1996 |
| WO | 96/40742 | 12/1996 |

OTHER PUBLICATIONS

Atlas of Protein Sequence and Structure, vol. 5. Natl. Biomedical Research Foundation, Washington, p. 96, Jan. 1972.*

M. Constanzo et al., *Journal of Medicinal Chemistry*, 39:16:3039–3043, 1996.
P. Edwards et al., *Journal of Medicinal Chemistry*, 38:1:76–85, 1995.
S Tsutsumi et al., *Journal of Medicinal Chemistry*, 37:21:3492–3502, 1994.
D.M. Jones, *Letters in Peptide Science*, 2:3–4:147–154, 1995.
S. Lewis et al., *Thrombosis and Haemostasis*, 74:4:1107–1112, 1995.
D.M. Jones, *J. Enzyme Inhibition*, 9:43–60, 1995.

* cited by examiner

Primary Examiner—Michael Borin
(74) Attorney, Agent, or Firm—Rothwell, Figg, Ernst & Manbeck, p.c.

(57) ABSTRACT

The invention relates to non-slow-binding thrombin inhibitors of the formula: A—B—C-Lys-D wherein A is H, 2-hydroxy-3-cyclohexylpropionyl-, $R_1$, $R_1$—O—CO—, $R_1$—CO—, $R_1$—$SO_2$—, —$(CHR_2)_n COOR_3$, or an N-protecting group, wherein $R_1$ is selected from —(1–6C)alkylene-COOH, (1–12C)alkyl, (2–12C)alkenyl, (6–14C)aryl, (7–15C)aralkyl; and (8–16C)aralkenyl, the aryl group of which may be substituted with (1–6C)alkyl, (2–12C) alkoxy, hydroxy, or halogen; $R_2$ is H or has the same meaning as $R_1$, $R_3$ is selected from H, (1–12C)alkyl, (2–12C)alkenyl, (6–14C)aryl, (7–15C)aralkyl and (8–16C) aralkenyl, the aryl group of which may be substituted with (1–6C)alkyl, (2–12C)alkoxy, hydroxy or halogen; n is an integer of 1 to 3; B is a bond, L-Asp or an ester derivative thereof, Leu, norLeu, —N(benzyl)-$CH_2$—CO—, —N(2-indane)-$CH_2$—CO—, D-1-Piq, D-3-Piq, D-Tiq, Atc or a D-amino acid having a hydrophobic aromatic side chain; C is Azt, Pro, Pec, norLeu(cyclo)Gly, an amino acid of one of the formulae —N[(3–8C)cycloalkyl]-$CH_2$—CO— or —N(benzyl)-$CH_2$—CO—, D is selected from COOH, tetrazole, oxazole, thiazole and benzothiazole, or A and C have the aforesaid meanings, B is D—(3–8C) cycloalkylalanine, and D is tetrazole, oxazole, thiazole or benzothiazole; or a prodrug thereof; or a pharmaceutically acceptable salt thereof; with the exception of the compound Me-D-Phe-Pro-Lys-COOH. The compounds can be used as antithrombotic agents.

8 Claims, No Drawings

THROMBIN INHIBITORS

The present invention relates to non-slow-binding thrombin inhibitors, a process for the preparation of said inhibitors, pharmaceutical compositions containing the same, and the use of these thrombin inhibitors as antithrombotic agents.

BACKGROUND OF THE INVENTION

Much attention has been focused on inhibition of thrombin as potential anticoagulants. Inhibitors of the enzyme thrombin, a key serine protease within the blood coagulation cascade, have for some time been considered as potential candidates for anticoagulant prophylaxis and therapy. In particular the multiple roles played by thrombin in its actions on coagulation factors, circulating blood components, and the cells of the vessel wall makes it a particularly attractive target in a variety of pathological states. Moreover, limitations associated with currently employed anticoagulants, in particular the occurrence of bleeding complications, necessitate the search for more specifically-acting agents.

Many peptide(-like) serine protease inhibitors have been disclosed, amongst which are transition state inhibitors of thrombin. Many of these latter compounds, however, are slow-binding inhibitors. The use of slow-binding inhibitors of thrombin is open to criticism. In vivo, thrombin is constantly generated in plasma and thrombin inhibitors primarily function by slowing thrombin formation through inhibiting thrombin-mediated amplification steps. To slow down such an amplification cascade, a non-slow-binding inhibitor would be preferable. A larger dose of a slow-binding inhibitor would be needed to achieve the same effect, with a correspondingly increased risk of side-effects.

Relevant thrombin inhibitors are disclosed by Brady et al., Bioorganic & Medicinal Chemistry, 3 (1995), 1063–78 wherein D-Phe-Pro-Arg-amide and D-Phe-Pro-Lys-X derivatives have been disclosed, X being a ketoester or amine. These compounds are disclosed to be slow-binding thrombin inhibitors, and likewise these compounds are excluded from the present invention. In the search for non-slow-binding thrombin inhibitors Jones et al., J. Enzyme Inhibition, 9 (1995), 43–60 attempted to obtain improvement by using D-Cha-Pro-Lys-COOH derivatives. However, although these derivatives proved to be more potent thrombin inhibitors, they still exhibit slow-binding properties.

In a recent attempt to obtain potent non-slow-binding thrombin inhibitors Lewis et al., Thrombosis and Haemostasis, 74(4) (1995), 1107, prepared Me-D-Phe-Pro-Lys-X derivatives, X being carboxyamide or carboxylic acid. These compounds, among which specifically disclosed Me-D-Phe-Pro-Lys-COOH, are classified as slow-binding inhibitors. This compound therefore does not fulfill the requirements of the present invention and is excluded from protection.

A thrombin inhibitor with an alkyl-substituted lysine is disclosed in U.S. Pat. No. 5,523,308. In earlier references other Phe-Pro-Lys sequences are described, for example by Iwanowicz et al. in Bioorganic & Medicinal Chemistry Letters, 2 (1992), 1607–12, which discloses D-Phe-Pro-Lys-X derivatives, X being i.a. a ketoester. Such compounds may also be described as slow-binding thrombin inhibitors.

Other types of peptides for inhibition of different serine proteases are also disclosed. Tsutsumi et al. in J. Med. Chem., 37 (1994), 3492–3502 described peptide-like compounds having thiazole and benzothiazole C-terminal ends. It was found that such thiazole derivatives are 300 times more potent than the corresponding thiophene analogues. It was further posited that C-terminal heterocyclic groups would provide a critical hydrogen-bond interaction with the histamine of the protease prolyl endopeptidase. Although it was further suggested that this feature may well be capable of extension to other serine proteases, thrombin proteases were not specifically mentioned. The mechanistic explanation of Tsutsumi was later challenged by Edwards et al. in J. Med. Chem., 38 (1995), 76–85, but also these authors found that elastase inhibitors of the type D-Phe-Val-Pro-Val-X, X being thiazole and benzothiazole, are non-slow-binding inhibitors of the relevant serine protease. These authors suggest the development of peptidyl α-ketoheterocycles as inhibitors of other serine proteases as well.

SUMMARY OF THE INVENTION

The present invention relates to the surprising finding that the teachings of Edwards, Tsutsumi and others can also be applied to thrombin inhibitors. The application of the C-terminal heterocycles to the compounds as disclosed by Lewis, Jones and Brady provide potent thrombin inhibitors having non-slow-binding properties to thrombin. Moreover, many of these compounds show improved biological half-lifes and oral bioavailability.

The invention therefore relates to non-slow-binding thrombin inhibitors of the formula:

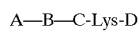

wherein
A is H, 2-hydroxy-3-cyclohexyl-propionyl-, $R_1$, $R_1$—O—CC—, $R_1$—CO—, $R_1$—SO$_2$—, —(CHR$_2$)$_n$COOR$_3$, or an N-protecting group, wherein
 $R_1$ is selected from —(1–6C)alkylene-COOH, (1–12C) alkyl, (2–12C)alkenyl, (6–14C)aryl, (7–15C)aralkyl and (8–16C)aralkenyl, the aryl group of which may be substituted with (1–6C)alkyl, (2–12C)alkoxy, hydroxy, or halogen;
 $R_2$ is H or has the same meaning as $R_1$;
 $R_3$ is selected from H, (1–12C)alkyl, (2–12C)alkenyl, (6–14C)aryl, (7–15C)aralkyl and (8–16C)aralkenyl, the aryl group of which may be substituted with (16C)alkyl, (2–12C)alkoxy, hydroxy, or halogen;
 n is an integer of 1 to 3;
B is a bond, L-Asp or an ester derivative thereof, Leu, norLeu, —N(benzyl)—CH$_2$—CO—, —N(2-indane)—CH$_2$—CO—, D-1-Piq, D-3-Piq, D-Tiq, Atc or a D-amino acid having a hydrophobic aromatic side chain;
C is Azt, Pro, Pec, norLeu(cyclo)Gly, or an amino acid of one of the formulae —N[(3–8C)cycloallkyl]-CH$_2$—CO— or —N(benzyl)-CH$_2$—CO—;
D is selected from COOH, tetrazole, oxazole, thiazole and benzothiazole;
or A and C have the aforesaid meanings, B is D—(3–8C) cycloalkylalanine, and D is tetrazole, oxazole, thiazole or benzothiazole;
or a prodrug thereof,
or a pharmaceutically acceptable salt thereof;
with the exception of the compound Me-D-Phe-Pro-Lys-COOH.

The compounds of the present invention are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The compounds of the invention may also be used as anticoagulants in extracorporeal blood circuits, as necessary in dialysis and surgery. The compounds of the invention may also be used as in vitro anticoagulants.

DETAILED DESCRIPTION OF THE INVENTION

Preferred compounds according to this invention are the compounds wherein D is COOH. In addition, preferably A is H, (1–12C)alkyl, —CO—(7–15C)aralkyl, —SO$_2$—(1–12C)alkyl, —SO$_2$—(6–14C)aryl, or —SO$_2$(7–15C)aralkyl; B is a bond, L-Asp, norLeu, D-1-Piq, or D-Phe; and C is Pro, norLeu(cyclo)Gly, or —N-cyclopentyl—CH$_2$—CO—. More preferred are the non-slow-binding thrombin inhibitors wherein A is —SO$_2$-benzyl, B is a bond, and C is norLeu(cyclo)Gly, or wherein A is —SO$_2$-ethyl, B is D-Phe, and C is Pro; or wherein A is hydrogen, B is D-1-Piq, and C is Pro.

Other preferred compounds according to the invention are those wherein D is oxazole or thiazole. Further, preferably A is H, (1–12C)alkyl, 2-hydroxy-3-cyclohexyl-propionyl-, —CO—(CH$_2$)$_n$COOH, —CO—(7–15C)aralkyl, —SO$_2$—(6–14C)aryl, —SO$_2$—(7–15C)aralkyl, —SO$_2$—(1–12C)alkyl, —(CHR$_2$)$_n$COOR$_3$, R$_2$ being H or (1–12Calkyl) and R$_3$ being H, (1–12C)alkyl or benzyl; and C is Pro, norLeu(cyclo)Gly, or —N[(3–8C)cycloalkyl]-CH$_2$—CO—. Particularly preferred are the non-slow-binding thrombin inhibitor wherein A is —(CH$_2$)$_n$COOR$_3$, R$_3$ being H, (1–12C)alkyl or benzyl; B is D—(3–8C)cycloalkylalanine, or D-Phe optionally monosubstituted with alkoxy or halogen; and C is Pro. The most preferred compounds of the invention are compounds wherein D is thiazole. Specifically preferred is the non-slow-binding inhibitor HOOC—CH$_2$D-Cha-Pro-Lys-(2-thiazolyl).

The N-protecting group as defined in the definition of moiety A is any N-protecting group as used in peptides. Suitable N-protecting groups can be found in T. W. Green and P. G. M. Wuts: Protective Groups in Organic Synthesis, Second Edition (Wiley, N.Y., 1991) and in The Peptides, Analysis, Synthesis, Biology, Vol. 3 E. Gross and J. Meienhofer, Eds., (Academic Press, New York, 1981).

Alkyl, as used herein, is a branched or unbranched alkyl group having 1 to 12 carbon atoms, such as methyl, ethyl, isopentyl, dodecyl, and the like.

The term (1–6C)alkylene means a branched or unbranched alkylene group having 1 to 6 carbon atoms, such as —(CH$_2$)$_m$— and m is 1 to 6, —CH(CH$_3$)—, —CH(CH$_3$)—(CH$_2$)—, etc. The preferred alkylene group is methylene.

Alkenyl is a branched or unbranched unsaturated alkenyl group having 2 to 12 carbon atoms. Examples are ethenyl, propenyl, allyl, and the like.

Aralkyl and aralkenyl groups are alkyl and alkenyl groups respectively, substituted by one or more aryl groups, the total number of carbon atoms being 7 to 15 and 8 to 16, respectively. Preferred aralkyl groups are e.g. of the formulae —(CH$_2$)$_p$—CH—(C6H$_5$)$_2$, p being 1 or 2, or —(CH$_2$)$_q$—C$_6$H$_5$ optionally substituted with halogen, q being 1,2 or 3.

Aryl in above-mentioned definition and in the definition of aryl, as used in the compound of the invention, is an aromatic moiety of 6 to 14 carbon atoms. The aryl group may further contain one or more hetero atoms, such as N, S, or O. Examples of aryl groups are phenyl, naphthyl, (iso)quinolyl, indanyl, and the like. Most preferred is the phenyl group. The aryl group may be substituted with on or more alkyl groups, preferably methyl, alkoxy groups, preferably methoxy, hydroxy, or halogen. The term halogen means fluorine, chlorine, bromine or iodine. Chlorine is the preferred halogen.

The terms D-1-Piq and D-3-Piq mean 1- and 3-carboxyperhydroisoquinoline, respectively. The term Tiq means 1,2,3,4-tetrahydroisoquinoline-carboxylic acid. Atc is 2-aminotetralin-2-carboxylic acid. The terms Azt and Pec mean 2-azetidine carboxylic acid and pipecolinic acid, repectively.

The term norLeu(cyclo)Gly means a structural fragment of the formula

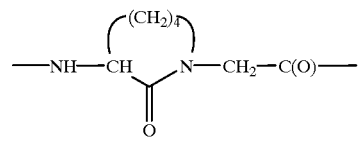

The term hydrophobic aromatic side chain means a (1–12C)alkyl substituted with one or more (6–14C)aryl groups (which may contain a heteroatom, e.g. nitrogen) such as phenyl, pyridinyl, naphthyl, tetrahydronaphthyl, and the like, which hydrophobic side chain may be substituted with hydrophobic substituents such as halogen (preferably chlorine), trifluoromethyl, lower alkyl (for instance methyl or ethyl), lower alkoxy (for instance methoxy), phenyloxy, benzyloxy, and the like.

The term (3–8C)cycloalkyl means cyclopropyl, cyclobutyl, cyclopentyl, cyclohexyl, cycloheptyl or cyclooctyl.

Tetrazole, oxazole, thiazole and benzothiazole have the following formulae, respectively:

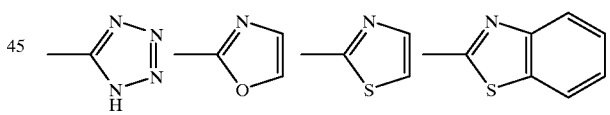

The invention also includes prodrugs of the compounds of the general formula, which after administration are metabolized into the active compounds. Suitable prodrugs are for example N-alkoxycarbonyl protected (preferably N-ethoxycarbonyl) derivatives of the general formula.

As used herein the term pharmaceutically acceptable salt refers to salts that retain the desired biological activity of the parent compound and preferably do not impart any undesired toxic effects. Examples of such salts are acid addition salts formed with inorganic acids, for example hydrochloric acid, hydrobromic acid, sulfuric acid, phosphoric acid nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts may be formed with polyvalent metal cations such as zinc, calcium, bismuth, barium, magnesium, aluminum, copper, cobalt, nickel and the like, or with an organic cation formed from N,N'-dibenzylethylenediamine or ethylenediamine, or combinations thereof (e.g. a zinc tannate salt).

The compounds of this invention possess one or more chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The invention further includes a process for preparing a compound of the formula, the process including coupling suitably protected amino acids or amino acid analogs, followed by removing the protecting groups.

The compounds according to the general formula may be prepared in a manner conventional for such compounds. To that end, suitably Na protected (and side-chain protected if reactive side-chains are present) amino acid derivatives or peptides are activated and coupled to suitably carboxyl protected amino acid or peptide derivatives either in solution or on a solid support. Protection of the α-amino functions generally takes place by urethane functions such as the acid-labile tert.-butyloxycarbonyl group (Boc), benzyloxycarbonyl (Z) group and substituted analogs or the base-labile 9-fluorenyl-methyloxycarbonyl (Fmoc). group. The Z group can also be removed by catalytic hydrogenation. Other suitable protecting groups include the Nps, Bmv, Bpoc, Aloc, MSC, etc. A good overview of amino protecting groups is given is given in The Peptides, Analysis, Synthesis, Biology, Vol. 3 E. Gross and J. Meienhofer, Eds., (Academic Press, New York, 1981). Protection of carboxyl groups can take place by ester formation e.g. base-labile esters like methyl or ethyl, acid labile esters like tert. butyl, or hydrogenolytically-labile esters like benzyl. Protection of side-chain functions like those of lysine can take place using the aforementioned groups. Activation of the carboxyl group of the suitably protected amino acids or peptides can take place by the azide, mixed anhydride, active ester, or carbodiimide method, especially with the addition of catalytic and racemization-suppressing compounds like 1-hydroxybenzotriazole, N-hydroxysuccinimide, 3-hydroxy4-oxo-3,4-dihydro-1,2,3,-benzotriazine, N-hydroxy-5-norbornene-2,3-dicarboximide. Also the anhydrides of phosphorus based acids can be used. See, e.g. The Peptides, Analysis, Synthesis, Biology, supra and Pure and Applied Chem. 59(3), 331–344 (1987).

It is also possible to prepare the compounds by the solid phase method of Merrifield. Different solid supports and different strategies are known see, e.g. Barany and Merrifield in The Peptides, Analysis, Synthesis, Biology, Vol. 2, E. Gross and J. Meienhofer, Eds., (Acad. Press, N.Y., 1980), Kneib-Cordonier and Mullen Int. J. Peptide Protein Res., 30, 705–739 (1987) and Fields and Noble Int. J. Peptide Protein Res., 35, 161–214 (1990).

Removal of the protecting groups, and, in the case of solid phase peptide synthesis, the cleavage from the solid support, can take place in different ways, depending on the nature of those protecting groups and the type of linker to the solid support. Usually deprotection takes place under acidic conditions and in the presence of scavengers. See, e.g. volumes 3, 5 and 9 of the series on The Peptides Analysis, Synthesis, Biology, supra.

Another possibility is the application of enzymes in synthesis of such compounds; for reviews see e.g. H. D. Jakubke in The Peptides, Analysis, Synthesis Biology, Vol. 9, S. Udenfriend and J. Meienhofer, Eds., (Acad. Press, N.Y., 1987).

However made, the compounds are useful for the manufacture of medicaments which have use in treating disease states involving undesired blood coagulation. In such a case the particular compound synthesized will typically be associated with a pharmaceutical carrier. Pharmaceutical carriers vary from things as relatively simple as sterilized water for injection to things as relatively complicated as microspheres and biodegradable implants.

As medicaments, the compounds are preferably administered orally, subcutaneously, topically, intranasally, intravenously, intramuscularly or locally (e.g. via an implant). Depot administration is also possible.

The exact dose and regimen for administration of these compounds and compositions will necessarily be dependent upon the needs of the individual subject to whom the medicament is being administered, the degree of affliction or need, and of course, the judgment of the medical practitioner. In general parenteral administration requires lower dosages than other methods of administration which are more dependent upon absorption. Illustratively however, the dosages are in the range of 0.001–100 mg per kg body weight, preferably 0.01–10 mg per kg body weight.

The medicament manufactured with the compounds may also be used as adjuvant in acute anticoagulant therapy. In such a case, the medicament is administered with other compounds useful in treating such disease states.

The compounds may also be used with implantable pharmaceutical devices such as those described in U.S. Pat. No. 4,767,628, the contents of which are incorporated by this reference. Then the device will contain sufficient amounts of compound to slowly release the compound (e.g. for more than a month).

Methods of making medicaments which can be adapted to contain the compound for enteral or parenteral administration are described in the standard reference, Gennaro et al., Remington's Pharmaceutical Sciences, (18th ed., Mack Publishing Company, 1990, see especially Part 8: Pharmaceutical Preparations and Their Manufacture), pages 1519 through 1580. Mixed with pharmaceutically suitable auxiliaries, the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is further explained by reference to the following illustrative Examples.

EXAMPLE 1

3,3-Diphenylpropionyl-Pro-Lys-(2-thiazolyl)

3,3-Diphenylpropionyl-prolyl-methylester

To a cold solution (0° C.) of 3,3-diphenylpropionic acid (5.0 g) in ethyl acetate (100 ml) were successively added DCCI (1,3-dicyclohexylcarbodiimide; 5.03 g), HOBt (1-hydroxy-benzotriazole hydrate; 3.28 g), H-Pro-OMe.HCl (3.66 g) and triethylamine (3.1 ml). The reaction mixture was stirred at 0° C. for 1 h and then kept at room temperature overnight. The reaction mixture was cooled to −20° C. and DCU (1,3-dicyclohexylurea) was removed by filtration. The filtrate was washed successively with 5% sodium hydrogencarbonate, water, 5% potassium hydrogensulfate and saturated aqueous sodium chloride; dried over sodium sulfate and concentrated in vacuo. The residue was purified by chromatography on silica (eluent: dichloromethane/ethyl acetate; 9/1 v/v) to yield 5.68 g of 3,3-diphenylpropionyl-prolylmethylester as a crystalline powder. TLC: $R_f$=0.75, silica gel, dichloromethane/ethyl acetate=7/3 v/v.

3,3-Diphenylpropionyl-prolyl-OH 3,3-Diphenylpropionyl-prolyl-methylester (5.6 g) dissolved in dioxane/water; 7/3 v/v (60 ml) was treated with a 4 M sodium hydroxide solution (6.2 ml) portionwise over 30 min at room temperature, keeping the pH at 10–10.5. After 30 min the reaction mixture was diluted with water (60 ml), a 4 M hydrochloric acid solution was added until pH 2.0 and the water layer was extracted with ethyl acetate. The combined organic phases were washed with water, saturated aqueous sodium chloride and dried over sodium sulfate and the solvent was removed by evaporation yielding 3,3-diphenylpropionyl-prolyl-OH as a syrup (5.18 g). TLC: $R_f$=0.65, silica gel, EPAW (ethyl acetate/pyridine/acetic acid/water) 63/20/6/11 v/v/v/v.

Boc-Lys(Cbz)-NMeOMe

Boc-Lys(Cbz)-OH.DCHA (10 g) was suspended in dichloromethane (200 ml). The suspension was washed with cold 0.1 N hydrochloric acid solution twice. 2-(1H-benzotriazol-1-yl)-1,1,3,3-tetramethyluronium tetrafluoroborate (6.0 g) and O,N-dimethyl-hydroxylamine hydrochloric acid (1.82 g) were added to the resulting organic phase and the pH was adjusted to pH 8 by adding triethylamine. The reaction mixture was stirred for 1 h at room temperature. The mixture was washed successively with cold 2N hydrochloric acid solution, water, 5% sodium hydrogencarbonate, and water. The organic layer was dried over sodium sulfate, filtered and evaporated. The residue was purified by chromatography on silica (eluent: dichloromethane/methanol; 5/5 v/v) to yield Boc-Lys(Cbz)-NMeOMe (7.2 g). TLC: $R_f$=0.55, silica gel, dichloromethane/ methanol 95/5 v/v.

Boc-Lys(Cbz)-(2-thiazolyl)

To a cold (−78° C.), stirred solution of n-butyllithium (63.9 mmol) in diethyl ether (58 ml), was added dropwise a solution of 2-bromothiazole (10.5 g) in diethyl ether (30 ml). The solution was stirred at −78° C. for 30 min, after which a solution of Boc-Lys(Cbz)-NMeOMe (8.2 g) in dry THF (tetrahydrofuran; 75 ml) was added slowly. The mixture was stirred at −78° C. for 1 h, then 5% aqueous sodium hydrogencarbonate was added. The mixture was allowed to warm to room temperature and the layers were separated. The aqueous layer was extracted with diethyl ether. The combined organic layers were washed with water, dried over sodium sulfate, filtered and evaporated. The residue was purified by chromatography on silica (eluent: ethyl acetate/heptane; 3/1 v/v) to yield Boc-Lys(Cbz)-(2-thiazolyl) (8.6 g). TLC: $R_f$=0.77, silica gel, ethyl acetate/heptane=3/1 v/v.

H-Lys(Cbz)-(2-thiazolyl).TFA

Boc-Lys(Cbz)-(2-thiazolyl) (500 mg) was dissolved in 50% TFA(trifluoroacetic acid)/dichloromethane (5 ml) and stirred for 1 h at room temperature. The crude H-Lys(Cbz)-(2-thiazolyl).TFA was isolated in quantitative yield after removal of the solvent by evaporation, and used immediately in the next step. TLC: $R_f$=0.25, silica gel, EPAW =63/20/6/11 v/v/v/v.

3,3-Diphenylpropionyl-Pro-Lys(Cbz)-(2-thiazolyl)

To a cold (0° C.) solution of 3,3-diphenylpropionyl-prolyl-OH (385 mg) in dimethyl formamide (5 ml) were successively added DCCI (270 mg), HOBt (176 mg), H-Lys (Cbz)-(2-thiazolyl).TFA (515 mg) and N-ethylmorpholine (0.28 ml). The reaction mixture was stirred at 0° C. for 1 h and then kept overnight at room temperature. The mixture was cooled to −20° C. and DCU was removed by filtration. The filtrate was evaporated to dryness. The residue was dissolved in ethyl acetate and washed successively with 5% aqueous sodium hydrogen-carbonate, water, 5% aqueous potassium hydrogensulfate and saturated aqueous sodium chloride, dried over sodium sulfate and concentrated in vacuo. The residue was purified by chromatography on silica (eluent: ethyl acetate/heptane; 4/1 v/v) to yield 3,3-diphenylpropionyl-Pro-Lys(Cbz)-(2-thiazolyl) (332 mg). TLC: $R_f$=0.40, silica gel, ethyl acetate/heptane; 3/1 v/v.

3,3-Diphenylpropionyl-Pro-Lys-(2-thiazolyl)

3,3-Diphenylpropionyl-Pro-Lys(Cbz)-(2-thiazolyl) (320 mg) was treated with TFA/thioanisole 10/1 v/v (3.3 ml) for 3 h at room temperature. The reaction mixture was concentrated in vacuo and the residue was dissolved in water. The aqueous phase was washed extensively with diethyl ether.

The water layer, containing 3,3-diphenylpropionyl-Pro-Lys-(2-thiazolyl) was charged directly onto a preparative HPLC Supelcosil LC-18-DB column using a gradient elution system of 20% A/60% B/20% C to 20% A/80% C over 45 min, at a flow rate of 20 ml/min. (A: 0.5 M sodium phosphate buffer pH 2.1, B: water, C: acetonitrile/water; 3/2 v/v).

Yield: 47 mg of 3,3-diphenylpropionyl-Pro-Lys-(2-thiazolyl). TLC: $R_f$=0.57, silica gel, EPAW; 63/20/6/11 v/v/v/v. $R_t$ (LC): 32.9 min 20% A/60% B/20% C to 20% A/0% B/80/% C in 40 min.

EXAMPLE 2

In a similar manner as described in Example 1 were prepared:

(a). H—D-Phe-ProLys-(2-thiazolyl)

$R_t$ (LC): 25.67 min; 20% A/80% B/0% C to 20% A/20% B/60% C in 40 min.

(b). H—D-1-Tiq-Pro-Lys-(2-thiazolyl)

$R_t$ (LC): 23.40 min; 20% A/80% B/0% C to 20% A/20% B/60% C in 40 min. (Tiq=tetrahydroisoquinolin)

(c). H—D—(p—Cl)-Phe-Pro-Lys-(2-thiazolyl)

$R_t$ (LC): 30.47 min; 20% A/80% B/0% C to 20% A/20% B/60% C in 40 min.

(d). Indaneglycyl-(N-cyclopropyl)-Gly-Lys-(2-thiazolyl)

$R_t$ (LC): 27.88 min; 20% A/80% B/0% C to 20% A/20% B/60% C in 40 min.

(e). H—D-Phe-(N-cyclopentyl)-Gly-Lys-(2-thiazolyl)

$R_t$ (LC): 31.07 min; 20% A/80% B/0% C to 20% A/20% B/60% C in 40 min.

(f). Acetyl-D-Phe-(N-cyclopropyl)-Gly-Lys-(2-thiazolyl)

$R_t$ (LC): 33.73 min; 20% A/80% B/0% C to 20% A/20% B/60% C in 40 min.

(g). H—D-Cha-Pro-Lys-(2-thiazolyl)

$R_t$ (LC): 30.59 min; 20% A/80% B/0% C to 20% A/20% B/60% C in 40 min. (Cha=cycdohexylalanine)

(h). H—D-Phe-(N-cyclopropyl)Gly-Lys-(2-thiazolyl)

$R_t$ (LC): 5.1 min isocratic; 55/45 MeOH/25 mM phosphate pH=7.

(i). 3,3-Diphenylpropionyl-(N-cyclopropyl)-Gly-Lys-(2-thiazolyl)

$R_t$ (LC): 8.1 min isocratic; 75/25 MeOH/25 mM phosphate pH=7.

(j). H—D-Phe-(N-cyclobutyl)-Gly-Lys-(2-thiazolyl)

$R_t$ (LC): 30.59 min; 20% A/80% B/0% C to 20% A/20% B/60% C in 40 min.

(k). H-Atc-Pro-Lys-(2-thiazolyl)

$R_t$ (LC): 27.79+28.04 min; 20% A/80% B/0% C to 20% A/20% B/60% C in 40 min. (Atc=2-aminotetralin-2-carboxylic acid)

(l). H—D-Phe-(N-benzyl)-Gly-Lys-(2-thiazolyl)

$R_t$ (LC): 16.99 min; 20% A/60% B/20% C to 20% A/0% B/80% C in 40 min.

(m). H—D—Cha-(N-cyclopropyl)-Gly-Lys-(2-thiazolyl)

$R_t$ (LC): 30.84 min; 20% A/80% B/0% C to 20% A/20% B/60% C in 40 min.

(n). p-chloro-3-phenylpropionyl-(N-cyclopentyl)-Gly-Lys-(2-thiazolyl)

$R_t$ (LC): 36.15 min; 20% A/60% B/20% C to 20% A/0% B/80% C in 40 min.

(o). (N-benzyl)-Gly-(N-cyclopentyl)-Gly-Lys-(2-thiazolyl)

$R_t$ (LC): 28.14 min; 20% A/80%B/0% C to 20%A/80% C in 40 min.

EXAMPLE 3

HOOC—CH$_2$—D-Cha-(N-cyclopentyl)-Gly-Lys-(2-thiazolyl)

N-Cyclopentyl-Gly-OMe

To a solution of 23.2 g of H-Gly-OMe.HCl in 200 ml of methanol was added 15.6 g of cyclopentanone. The mixture was stirred for 15 min. and 7 g of sodium cyanoborohydride was added. The pH was adjusted to 6. The reaction mixture was stirred for 16 h at room temperature. To complete the reaction 1 g of cyclopentanone was added and stirring was continued. The reaction was monitored on TLC. When all the starting material had dissappeared, the mixture was acidified to pH 2 and stirred for 30 min. The solvent was removed and the residue diluted with water. The solution was washed with ether, the pH adjusted to 12 with 6N sodium hydroxide and extracted with dichloromethane. The combined organic layers were washed with saturated sodium chloride solution, dried on sodium sulfate and evaporated in vacuo to yield 16 g of an oil.

$R_f$=0.46 in ethyl acetate/pyridine/acetic acid/water 63/20/6/11 v/v/v/v on silica.

N-(t-butyloxycarbonyl-methyl)-D-Cha-OMe

To a stirred solution of 26 g of H—D-Cha-OMe.HCl in 300 ml of acetonitrile was added 17 g of t-butyl-bromo acetate. The pH of the reaction was adjusted to 8.5 with diisopropylethylamine. The mixture was stirred for 16 h at room temperature and evaporated in vacuo. The residue was dissolved in dichloromethane and the solution was washed with water, dried on sodium sulfate and evaporated in vacuo. Chromatography over silica gel in hexane:ethyl acetate 9:1 v/v gave 20 g of the title product.

$R_f$=0.46 in ethyl acetate/pyridine/acetic acid/water 15.75/5/1.5/2.75 v/v/v/v on silica.

N,N-Boc,(t-butyloxycarbonyl-methyl)-D-Cha-OMe

The pH of a solution of 20 g of N-(t-butyloxy-methyl)-D-Cha-OMe and 17 g of di-t-butyl dicarbonate was adjusted to pH 8.5 with diisopropylethylamine. The mixture was stirred for 16 h at room temperature. The solvent was removed in vacuo. To the residue was added dichloromethane and water. The organic layer was separated, washed with cold 1N hydrogen chloride, water, 5% sodium hydrogencarbonate and water. The organic layer was dried on sodium sulfate and the filtrate was evaporated to an amorphous solid with a yield of 28 g.

$R_f$=0.60 in ethyl acetate/pyridine/acetic acid/water 252/20/6/11 v/v/v/v on silica.

N,N-Boc,(t-butyloxycarbonyl-methyl)-D-Cha-OH

A solution of 28 g of N,N-Boc,(t-butylcarbonyl-methyl) D-Cha-OMe in 420 ml of dioxane:water 9/1 was treated with sufficient 1N sodium hydroxide to keep the pH at 13 for 90 min. at room temperature. After acidification, the mixture was poured into water and extracted with dichloromethane. The organic layer was washed with water and dried on sodium sulfate. The filtrate was evaporated and yielded 24 g of the title compound.

$R_f$=0.23 in dichloromethane/methanol 9/1 v/v on silica.

N,N-Boc,(t-butyloxycarbonyl-methyl)-D-Cha-(N-cyclopentyl)-Gly-OMe

To a solution of 24 g of N,N-Boc,(t-butyloxycarbonyl-methyl)-D-Cha-OH in 300 ml of N,N-dimethylformamide was added 10.2 g N-cyclopentyl-Gly-OMe and 21.2 g of 2-(1H-benzotriazol-1-yl)-1,1,3,3-tetramethyluronium tetrafluoroborate (TBTU).

The pH of the mixture was adjusted to 8.5. The mixture was stirred overnight at room temperature and concentrated by evaporation. Water and ethyl acetate were added to the residue. The organic layer was separated and washed with 1N hydrogen chloride, water, 5% sodium hydrogencarbonate and water and dried over sodium sulfate. The filtrate was evaporated and the residue was chromatographed on silica gel in hexane:ethyl acetate 8:2 as eluent. The fractions containing the title product are pooled and evaporated. Yield: 17 g. Rf=0.57 in hexane/ethyl acetate 7/3 v/v on silica.

N,N-Boc,(t-butyloxycarbonyl-methyl)-D-Cha-(N-cyclopentyl)-Gly-OH

Using the same procedure as for N,N-Boc,(t-butyloxycarbonyl-methyl)-D-Cha-OH, 17 g of N,N-Boc,(t-butyloxycarbonyl-methyl)-D-Cha-(N-cyclopentyl)-Gly-OMe is saponified and yielded 15 g of an amorphous solid. Chromatography over silica gel with dichloromethane/methanol 95/5 v/v as eluent gave 13 g of the title compound.

Rf=0.30 in methylene chloride/methanol 9/1 v/v on silica.

HOOC—CH$_2$—D-Cha-(N-cyclopentyl)-Gly-Lys-(2-thiazolyl)

Using N,N-Boc,(t-butyloxycarbonyl-methyl)-D-Cha-(N-cyclopentyl)-Gly-OH in similar procedures as described for example 1, this compound was prepared.

Rt (LC): 23.57 min; 20% A, 60% B, 20% C to 20% A, 80% C in 40 min.

(a). In a similar manner as described above using Proline.HCl and HONSu (as in example 11) HOOC—CH$_2$—D-Cha-Pro-Lys-(2-thiazolyl) was prepared. Rt (LC): 31.44 min; 20% A, 80% B, 0% C to 20% A, 20% B, 60% C in 40 min.

EXAMPLE 4

3-Phenylpropionyl-Pro-LysΨ[COCO]—OH

Boc-Lys(Cbz)-OMe

Boc-Lys(Cbz)-OH (25 g) was dissolved in dichloromethane/methanol=9/1 v/v (500 ml). TBTU (21.1 g) was added and the solution adjusted to pH 8 by addition of triethylamine. The reaction mixture was stirred for 1 h at room temperature. The mixture was washed successively with cold 2N hydrogen chloride solution, water, 5% sodium hydrogencarbonate, and water. The organic layer was dried over sodium sulfate, filtered and evaporated. The residue was purified by chromatography on silica (eluent: ethyl acetate/heptane =1/4 v/v) to yield Boc-Lys(Cbz)-OMe (26.7 g). TLC: R$_f$=0.79, silica gel, ethyl acetate/heptane=3/1 v/v.

Boc-Lys(Cbz)Ψ[cyanoacetate]

To a cold (−78° C.) solution of Boc-Lys(Cbz)-OMe (20 g) in dry dichloromethane (600 ml) was added dropwise diisobutyl aluminumhydride (127 ml of 1M solution in hexane) at a rate to keep the reaction temperature below −70° C. The resulting solution was stirred at −78° C. for 30 min. A 5% citric acid solution (500 ml) was added to the reaction mixture. The two layer mixture was stirred at room temperature for 10 min, the layers were separated and the aqueous layer was extracted twice with dichloromethane. The combined dichloromethane layers were washed with water and dried over sodium sulfate and filtered. The solution was placed under nitrogen and cooled on a icewaterbath. A solution of sodium cyanide (24.85 g) and benzyltriethyl ammonium chloride (2.89 g) in water (500 ml) was added. Under vigorous stirring acetic anhydride was added portionwise (6×6 ml) over a period of 30 min. The organic layer was separated and the aqueous layer was extracted twice with dichloromethane. The combined dichloromethane layers were washed with water, dried over sodium sulfate, filtered and evaporated in vacuo. The residue was purified by chromatography on silica (eluent: dichloromethane/ethyl acetate=9/1 v/v) to yield Boc-Lys(Cbz)Ψ[cyanoacetate] (17.2 g.). TLC: R$_f$=0.60, silica gel, dichloromethane/ethyl acetate=7/3 v/v.

Boc-Lys(Cbz)Ψ[CHOHCO]—OMe

A solution of Boc-Lys(Cbz)Ψ[cyanoacetate] (17.2 g.) in diethyl ether/methanol=3/1 v/v (500 ml) was cooled to −20° C. under nitrogen, and 54.7 g of gaseous hydrochloric acid was introduced keeping the temperature below −5° C. The reaction mixture was kept at 4° C. overnight. Water (85 ml) was added dropwise to the reaction mixture keeping the temperature below 5° C. After stirring for 4 h at room temperature the organic layer was separated and washed with water. The aqueous layer was saturated with sodium chloride and extracted with sec-butanoldichloromethane=3/2 v/v. The organic phase was washed with brine, dried over sodium sulfate, filtered and evaporated in vacuo to give 17.4 g of the crude amine.

The residue was taken up in dimethyl formamide (DMF, 200 ml), bis-(tert-butyl)anhydride (8.7 g) was added and triethylamine until pH 8. The reaction mixture was stirred at room temperature overnight. The solvent was removed by evaporation at reduced pressure. The residue was dissolved in ethyl acetate, washed with water and brine successively, dried over sodium sulfate, filtered and evaporated in vacuo. The residue was purified by chromatography on silica (eluent: ethyl acetate/heptane=1/1 v/v) to yield Boc-Lys(Cbz)Ψ[CHOHCO]—OMe (6.22 g). TLC: R$_f$=0.75, silica gel, ethyl acetate/heptane=3/1 v/v.

3-Phenylpropionyl-Pro-Lys(Cbz)Ψ[CHOHCO]—OMe

Boc-Lys(Cbz)Ψ[CHOHCO]—OMe (60 mg.) was dissolved in 50% trifluoroacetic acid/dichloromethane (6 ml) and stirred for 1 h at room temperature. The crude amine was isolated in quantitative yield after removal of the solvent by evaporation, and used immediately to prepare 3-phenylpropionyl-Pro-Lys(Cbz)Ψ[CHOHCO]—OMe.

3-Phenylpropionyl-Pro-OH was dissolved in dry DMF (5 ml). After addition of triethylamine (196 ml), the reaction mixture was placed under nitrogen and cooled to —15° C. Isobutylchloroformate (183 ml) was subsequently added and the mixture was allowed to stir for 15 min at −15° C. The crude amine was dissolved in dry DMF (5 ml), neutralised using triethylamine and added dropwise to the cold mixed anhydride solution. The reaction stirred for 1 h at −15° C. and then kept at 0° C. overnight. The mixture was evaporated to dryness. The residue was dissolved in ethyl acetate and successively wsahed with water, 5% sodium hydrogencarbonate and brine, dried over sodium sulfate and concentrated in vacuo. The residue was purified by chromatography on silica (eluent: dichloromethane/methanol=95/5 v/v) to yield 3-phenylpropionyl-Pro-Lys(Cbz)Ψ[CHOHCO]—OMe (246 mg). TLC: R$_f$=0.92, silica gel, EPAW=63/20/6/11 v/v/v/v.

3-Phenylpropionyl-Pro-LysΨ[CHOHCO]—OMe

To a solution of 3-phenylpropionyl-Pro-Lys(Cbz)Ψ[CHOHCO]—OMe (240 mg) in methanol (5 ml) was added 10% palladium on charcoal (50 mg) and 216 ml 2N hydrogen chloride solution. The mixture was hydrogenated at atmospheric pressure and at room temperature for 1 h. The palladium catalyst was removed by filtration and the solvent removed by evaporation at reduced pressure yielding 3-phenylpropionyl-Pro-LysΨ[CHOHCO]—OMe quantitatively. TLC: R$_f$=0.13, silica gel, dichloromethane/methanol=9/1 v/v.

3-Phenylpropionyl-Pro-Lys(Boc)Ψ[CHOHCO]—OMe

To a solution of phenylpropionyl-Pro-LysΨ[CHOHCO]—OMe (196 mg.) in dry DMF (5 ml) was added bis(tert-butyl)anhydride (102 mg) and the pH was adjusted to pH 8.5 by adding triethylamine. The reaction mixture was stirred at room temperature overnight. The mixture was evaporated in vacuo and the resulting residue was purified by chromatography on silica (eluent: dichloromethane/methanol=98/2 v/v to yield 3-phenylpropionyl-Pro-Lys (Boc)Ψ[CHOHCO]—OMe (189 mg). TLC: $R_f$=0.43, silica gel, dichloromethane/methanol=9/1 v/v.

3-Phenylpropionyl-Pro-Lys(Boc)Ψ[CHOHCO]—OH

Phenylpropionyl-Pro-Lys(Boc)Ψ[CHOHCO]—OMe (185 mg.) was dissolved in dioxane/water=7/3 (5 ml) and treated with 2M sodium hydroxide solution (267 ml) portionwise over 30 min at room temperature, keeping the pH at 10–10.5. After 30 min the reaction mixture was diluted with water (20 ml), 2M hydrogen chloride solution was added until pH 2.0 and the water layer was extracted with dichloromethane. The combined organic phases were washed with water (50 ml), brine (50 ml) and dried over sodium sulfate, filtered and concentrated in vacuo to yield 3-phenylpropionyl-Pro-Lys(Boc)Ψ[CHOHCO]—OH (228 mg). TLC: $R_f$=0.60, silica gel, EPAW=63/20/6/11 v/v/v/v.

3-Phenylpropionyl-Pro-Lys(Boc)Ψ[COCO]—OH

To a solution of phenylpropionyl-Pro-Lys(Boc)Ψ[CHOHCO]—OH (220 mg) in dry dichloromethane (5 ml) were added 255 mg of periodinane (Dess-Martin reagent). After 1 h stirring at room temperature, 2% sodium thiosulfate solution was added (15 ml) and the mixture was stirred for 30 min at room temperature. The organic layer was separated, washed with water, dried over sodium sulfate, filtered and evaporated in vacuo to give crude keto-acid 3-phenylpropionyl-Pro-Lys(Boc)Ψ[COCO]—OH (411 mg). TLC: $R_f$=0.47, silica gel, EPAW=63/20/6/11 v/v/v/v.

3-Phenylpropionyl-Pro-LysΨ[COCO]—OH

3-Phenylpropionyl-Pro-Lys(Boc)Ψ[COCO]—OH (411 mg) was treated with 90% trifluoroacetic acid/water for 1 h at room temperature. The reaction mixture was concentrated in vacuo and the residue was dissolved in water and directly chraged onto a preparative HPLC Supelcosil LC-18-DB column using a gradient elution system of 20% A/70% B/10% C to 20% A/0% B/80% C over 45 min, at a flow rate of 20 ml/min. (A: 0.5M phosphate buffer pH 2.1, B: water, C: acetonitril/water=3/2). Yield: 71 mg. of 3-phenylpropionyl-Pro-LysΨ[COCO]—OH. $R_t$ (LC): 24.9 min; 20%A/80%B to 20%A/20%B/60%C in 40 min.

In a similar manner as described above were prepared:

(a). 3,3diphenylpropionyl-Pro-LysΨ[COCO]—OH $R_t$ (LC): 36.42 min; 20% A/80% B/0% C to 20% A/20% B/60% C in 40 min.

(b). 3-Phenylpropionyl-(N-cyclopentyl)-Gly-LysΨ[COCO]—OH $R_t$ (LC): 34.29 min; 20% A/80% B/0% C to 20% A/20% B/60% C in 40 min.

(c). 3-[(p—Cl)-phenyl]propionyl-(N-cyclopentyl)-Gly-LysΨ[COCO]—OH $R_t$ (LC): 39.52 min; 20% A/80% B/0% C to 20% A/20% B/60% C in 40 min.

(d). 3-[(p—Cl)-phenyl]propionyl-Pro-LysΨ[COCO]—OH $R_t$ (LC): 31.31 min; 20% A/80% B/0% C to 20% A/20% B/60% C in 40 min.

(e). Naphthylsulfonyl-Asp-Pro-LysΨ[COCO]—OH $R_t$ (LC): 30.45 min; 20% A/80% B/0% C to 20% A/20% B/60% C in 40 min.

EXAMPLE 5

H—D-Cha-Pro-Lys-(2-benzothiazolyl)

Boc-Lys(Cbz)-Ψ[CHOH]-(2-benzothiazolyl)

To a cold (−78° C.) solution of Boc-Lys(Cbz)-OMe (1 g) in dichloromethane (25 ml) was added dropwise diisobutyl aluminumhydride (DiBAL-H; 7.6 ml of a 1M solution in hexane) whereby the reaction temperature was kept below −70° C. The resulting solution was stirred at −78° C. for 30 min. A 5% citric-acid solution was added to the reaction mixture. The two layers mixture was stirred at room temperature for 10 min, the layers were separated and the aqueous layer is was extracted twice with dichloromethane. The combined dichloromethane layers were washed with water, 5% sodium hydrogencarbonate, water and dried over sodium sulfate and filtered. The solution was placed under nitrogen and 2-(trimethylsilyl)benzothiazole (0.79 g) was added and the reaction mixture was stirred for 16 h at room temperature. After evaporation to dryness the residue was dissolved in dry tetrahydrofuran (15 ml) and tetrabutyl ammoniumfluoride (3.8 ml of a 1M solution in THF) was added. The mixture was stirred for 2 h at room temperature and water was added. The product was extracted with dichloromethane and purified by chromatography on silica (eluent: dichloromethane/ethyl acetate; 9/1 v/v) to yield 724 mg of Boc-Lys(Cbz)-Ψ[CHOH]-(2-benzothiazolyl). TLC: $R_f$=0.35, silica gel, dichloromethane/ethyl acetate=7/3 v/v.

Boc-Lys(Cbz)-(2-benzothiazolyl)

To a solution of Boc-Lys(Cbz)-Ψ[CHOH]—(2-benzothiazolyl) (700 mg) in dry dichloromethane (10 ml) was added 1 g. of periodinane (Dess-Martin reagent). After stirring for 1 h at room temperature, 2% sodium thiosulfate solution was added and the mixture was stirred for another 30 min at room temperature. The organic layer was separated, washed with water, dried over sodium sulfate, filtered and evaporated in vacuo. The residue was purified by chromatography on silica (eluent: ethyl acetate/heptane; 3/1 v/v) to yield 193 mg of Boc-Lys(Cbz)-(2-benzothiazolyl). TLC: $R_f$=0.85, silica gel, ethyl acetate/heptane=3/1 v/v.

Boc-D-Cha-Pro-Lys(Cbz)-(2-benzothiazolyl)

Boc-Lys(Cbz)-(2-benzothiazolyl) (193 mg) was dissolved in 50% TFA/dichloromethane (2 ml) and stirred for 1 h. at room temperature. The crude amine was isolated in quantitative yield after removal of the solvent by evaporation, and used immediately to prepare Boc-D-Cha-Pro-Lys(Cbz)-(2-benzothiazolyl). Boc-D-Cha-Pro-OH was dissolved in dry dimethylformamide (4 ml). After addition of diisopropyl-ethylamine (DIPEA, 66 ml), the reaction mixture was placed under nitrogen and cooled to −15° C. Isobutylchloroformate (50 ml) was subsequently added and the mixture was allowed to stir for 15 min at −15° C. The crude amine was dissolved in dry DMF (4 ml), neutralised using diisopropy-lethylamine and added dropwise to the cold mixed anhydride solution. The reaction was stirred for 1 h at −15° C. and then kept at 0° C. overnight. The mixture was evaporated to dryness. The residue was dissolved in ethyl acetate and successively washed with water, 5% sodium hydrogencarbonate, water and brine, dried over sodium sulfate and concentrated in vacuo. The residue was purified by chromatography on silica (eluent: ethyl acetate/heptane; 1/1 v/v) to yield Boc-D-Cha-Pro-Lys(Cbz)-(2-benzothiazolyl) (191 mg). TLC: $R_f$=0.66, silica gel, ethyl acetate/heptane=3/1 v/v.

H—D-Cha-Pro-Lys-(2-benzothiazolyl)

Boc-D-Cha-Pro-Lys(Cbz)(2-benzothiazolyl) was treated with trifluoroacetic acid/thioanisole 10/1 v/v (2.2 ml) for 3.5 h at room temperature. The reaction mixture was concentrated in vacuo and the residue was dissolved in water. The aqueous phase was washed extensively with diethyl ether. The water layer, containing H—D-Cha-Pro-Lys-(2-benzothiazolyl) was charged directly onto a preparative HPLC Supelcosil LC-18-DB column using a gradient elution system of 20% A/80% B to 20% A/20% B/60% C over 40 min, at a flow rate of 20 ml/min. (A: 0.5 mM sodium phosphate buffer pH 2.1, B: water, C: acetonitrile/water; 3/2 v/v). Yield: 98 mg of H—D-Cha-Pro-Lys-(2-benzothiazolyl). $R_t$ (LC): 42 min 20% A/80% B to 20% A/20% B/60% C in 40 min.

EXAMPLE 6

H-D-Cha-Pro-Lys-(2-tetrazolyl)

Boc-Lys(Cbz)Ψ(CHOAc)-(2-tetrazolyl)

To a solution of Boc-Lys(Cbz)Ψ[cyanoacetate] (5.4 g) in 39 ml dimethylformamide was added 801 mg of ammonium chloride and 975 mg of sodium azide. The reaction mixture was heated to 80° C. and stiffed under nitrogen during 48 h. Precipitated salt was filtered off and the solution was evaporated under reduced pressure to dryness. This yielded 4.9 g of the desired compound. TLC: Rf=0.42, silica gel, toluene/ethanol=6/4 v/v.

Boc Lys(Cbz)Ψ(CHOH)-(2-tetrazolyl)

Boc-Lys(Cbz)Ψ(CHOAc)-(2-tetrazolyl) (1.25 g) was dissolved in 60 ml of dioxane/water 7/3 and 2.65 ml of a 2N sodium hydroxide solution was added. The solution was stirred at room temperature during 2.5 h after which the reaction appeared completed. The pH was adjusted to 5 and the resulting mixture was evaporated to dryness under reduced pressure. The residue was dissolved in methanol/dichloromethane 1/1 and insoluble salt was filtered off. This resulted in 1.27 g of the deacetylated product. TLC: Rf=0.40, silica gel, toluene/ethanol=6/4 v/v.

Boc-Lys(Cbz)-(2-tetrazolyl)

To a solution of 0.56 g of Boc-Lys(Cbz)Ψ(CHOH)-(2-tetrazolyl) in 37 ml dry dichloromethane, 1.38 g of Dess-Martin periodane reagent was added. The mixture was stirred at room temperature for 30 minutes after which the reaction was quenched with a 10% sodium thiosulfate solution in water. The organic layer was extracted with water and sodium hydrogencarbonate (5% in water). the water layers were combined en extracted with 1-butanol. The 1-butanol layer was evaporated to dryness under reduced pressure. The residue was chromatographed on a silica gel column using the eluent: ethyl acetate/pyridine/acetic acid/water=263/20/6/11 v/v/v/v. Yield: 0.22 g. TLC: Rf=0.30, silica gel, ethyl acetate/pyridine/acetic acid/water=63/20/6/11 v/v/v/v.

H-Lys(Cbz)-(2-tetrazolyl).TFA

Boc-Lys(Cbz)-(2tetrazolyl) (0.21 g) was dissolved in 16 ml trifluoroacetic acid/water 9/1. The mixture was stirred for 1 h at room temperature after which the solution was concentrated in vacuo to yield an oil. Yield: 0.34 g, used immediately to prepare tripeptide Boc-D-Cha-Pro-Lys (Cbz)-(2-tetrazolyl).

Boc-D-Cha-Pro-Lys(Cbz)-(2-tetrazolyl)

Boc-D-Cha-Pro-OH (0.19 g) was prepared according to the procedure described in example 1 for the dipeptide moiety. The coupling to H-Lys(Cbz)-(2-tetrazolyl) (0.17 g) was performed in a similar manner as described in example 5. Purification on silica gel (eluent: ethyl acetate/pyridine/acetic acid/water=163/20/6/11 v/v/v/v) yielded 0.21 g of the desired compound. TLC: Rf=0.17, silica gel, ethyl acetate/pyridine/acetic acid/water=63/20/6/11 v/v/v/v.

H—D-Cha-Pro-Lys-(2-tetrazolyl)

The removal of the protective groups and the HPLC purification was performed in an analogous procedure as described for example 5. Yield: 20 mg.

Rt (LC): 23.3 and 24.5 min, 20% A, 80% B to 20% A, 20% B and 60% C in 40 min.

EXAMPLE 7

HOOC—CH₂—CO—D-Cha-Pro-Lys-(2-thiazolyl)

H—D-Cha-Pro-Lys(Cbz)(2-thiazolyl).TFA

Boc-D-Cha-Pro-Lys(Cbz)-(2-thiazolyl) was prepared according to the procedure described for example 5. 0.30 g of this tripeptide was dissolved in 3 ml of trifluoroacetic acid/dichloromethane 1/1 v/v and the solution was stirred for 1 h at room temperature. The solution was evaporated to dryness under reduced pressure and coevaporated three times with toluene. Yield: quantitative, oil, used immediately for the next step. TLC: Rf=0.30, silica gel, ethyl acetate/pyridinelacetic acid/water=163/20/6/11 v/v/v/v.

(t-butyl-OOC—CH₂—CO)—D-Cha-Pro-Lys(Cbz)-(2-thiazolyl)

H—D-Cha-Pro-Lys(Cbz)2-thiazolyl).TFA (0.33 g) was dissolved in 3 ml of dry dichloromethane and 76 mg of mono-tertiary butyl malonate was added and the pH was adjusted to approximately 8 with triethylamine. Next, benzotriazolyloxytris(dimethylamino)-phosphonium hexafluorophosphate (211 mg) was added and the reaction mixture was stirred at room temperature for 2 h and at 4° C. for the next 16 h. The solution was concentrated in vacuo, dissolved in ethyl acetate and washed three times with water and brine. The organic layer was again concentrated in vacuo after being dried on magnesium sulfate. The residue was chromatographed on silica using heptane/ethyl acetate 2/8 v/v as eluent. This yielded 270 mg of the acylated tripeptide. TLC: Rf=0.21, silica gel, heptane/ethyl acetate=8/2 v/v.

HOOC—CH₂—CO—D-Cha-Pro-Lys-(2-thiazolyl)

The removal of the protective groups and the HPLC purification were performed in an analogous procedure as described for example 5. Yield: 124 mg.

Rt (LC): 38.23 min, 20% A, 80% B to 20% A, 20% B and 60% C in 40 min.

EXAMPLE 8

HOOC—(CH₂)₂CO—D-Cha-Pro-Lys-(2-thiazolyl)

(HOOC—(CH₂)₂—CO)—D-Cha-Pro-Lys(Cbz)-(2-thiazolyl)

H—D-Cha-Pro-Lys(Cbz)-(2-thiazolyl).TFA (0.33 g) was dissolved in 3 ml of dry dichloromethane and 0.335 ml of pyridine. To this solution 48 mg of succinic anhydride was added and the resulting solution was stirred at room temperature under nitrogen. After 4 h the reaction appeared completed and was quenched with a few droplets of water. The mixture was concentrated in vacuo, dissolved in ethyl acetate, washed with diluted acid, water and brine and dried on magnesium sulfate. After removal of the salt the organic layer was concentrated in vacuo which resulted in 320 mg of an oil.

TLC: Rf=0.37, silica gel, dichloromethane/methanol 9/1 v/v.

HOOC—(CH$_2$)$_2$—CO—D-Cha-Pro-Lys-(2-thiazolyl)

The removal of the protective groups and the HPLC purification were performed in an analogous procedure as described for example 5. Yield: 187 mg.

Rt (LC): 38.31 min 20% A, 80% B to 20% A, 20% B and 60% C in 40 min.

EXAMPLE 9

HOOC—CH(CH$_3$)—D-Cha-Pro-Lys-(2-thiazolyl)

(t-Butyl-OOC—CH(CH$_3$))—D-Cha-Pro-Lys(Cbz)-(2-thiazolyl)

H—D-Cha-Pro-Lys(Cbz)-(2-thiazolyl).TFA (0.33 g) was dissolved in 2 ml of acetonitril. Next, 0.50 g of 2-bromopropionic acid tert-butylester was added followed by 25 mg of sodium iodide. The pH of the solution was adjusted to 8 with diisopropylethylamine and kept at that basicity for 12 days at room temperature. The reaction mixture was concentrated in vacuo, dissolved in ethyl acetate, washed with water, dried on magnesium sulfate and again concentrated. The residue was chromatographed on silica using ethyl acetate/toluene 1/1 v/v as eluent. Yield: 279 mg. TLC: 0.75, silica gel, ethyl acetate.

HOOC—CH(H$_3$)—D-Cha-Pro-Lys-(2-thiazolyl)

The removal of the protective groups and the HPLC purification were performed in an analogous procedure as described for example 5. Yield: 40 mg and 29 mg (separated diastereomers). Rt (LC): 30.06 min and 34.87 min (separated diastereomers), 20% A, 80% B to 20% A, 20% B and 60% C in 40 min.

EXAMPLE 10

HOOC—(CH$_2$)$_2$—D-Cha-Pro-Lys-(2-thiazolyl) (t-Butyl-OOC—(CH$_2$)$_2$—D-Cha-Lys(Cbz)-(2-thiazolyl)

H—D-Cha-Pro-Lys(Cbz)-(2-thiazolyl).TFA (0.21 g) was dissolved in 5 ml of acetonitril. Next, 1.84 ml of acrylacid tert-butylester was added in three portions. The pH of the solution was adjusted to 8 with diisopropylethylamine and kept at that basicity for 13 days at room temperature. The reaction mixture was concentrated in vacuo, dissolved in ethyl acetate, washed with water, dried on magnesium sulfate and again concentrated. The residue was chromatographed on silica using ethyl acetate/toluene 2/1 v/v as eluent. Yield: 92 mg. TLC: Rf=0.62, silica gel, ethyl acetate.

HOOC—(CH$_2$)$_2$—D-Cha-Pro-Lys-(2-thiazolyl)

The removal of the protective groups and the HPLC purification were performed in an analogous procedure as described for example 5. Yield: 40 mg.

Rt (LC): 32.83 min, 20% A, 80% B to 20% A, 20% B and 60% C in 40 min.

EXAMPLE 11

N—Me—D-norLeu-Pro-Lys-(2-thiazolyl)

H—D-norLeu-OMe. HCl

To 270 ml of methanol, cooled to −15° C., 18.2 g of thionylchloride was added. Subsequently, the temperature was allowed to rise to −10° C. than kept constant for 20 min after which 10 g H—D-norLeu-OH was added. The temperature was slowly increased and at reflux kept constant for 5 h. The product was crystallized from methanol and diethyl ether at 4° C. and this yielded 12.9 g. TLC: Rf=0.61, silica gel, n-butanol/acetic acid/water 10/1/3 v/v/v.

Boc-D-norLeu-OMe

H—D-norLeu-OMe.HCl (12.9 g) was dissolved in 200 ml of dry methanol followed by addition of di-tert-butyl dicarbonate (15.5 g) and triethylamine (19.8 ml). The reaction was stirred for 3h at room temperature after which the mixture was concentrated in vacuo. Next, the residue was dissolved in ethyl acetate and washed with water. The product was chromatographed on silica using heptane/ethyl acetate 3/1 v/v . Yield: 16.9 g. TLC: Rf=0.55, silica gel, heptane/ethyl acetate 3/1 v/v.

N—Me-Boc-D-norLeu-OMe

Boc-D-norLeu-OMe (16.9 g) was dissolved in 200 ml of dry dimethylformamide under nitrogen. Next, methyliodide (24.9 ml) was added, cooled to 0° C., sodium hydride (3.31 g) was added and the mixture was allowed to react during 16 h at room temperature. The mixture was concentrated in vacuo, dissolved in ethyl acetate, washed with diluted hydrogen chloride (0.1 N), water, sodium hydrogencarbonate (5%) and water, dried and concentrated again. This yielded 18.8 g of alkylated product. TLC:=0.56, silica gel, heptane/ethyl acetate 3/1 v/v.

N—Me-Boc-D-norLeu-OH

N—Me-Boc-D-norLeu-OMe (18 g) was dissolved in 400 ml of dioxane/water 9/1 v/v and the pH of the solution was adjusted to 12 with 1N sodium hydroxide. The reaction was allowed to proceed for 2 h, keeping the pH constant at 12. The work-up procedure involved a pH adjustment to 2, cooling on ice, adding extra water (400 ml) and an extraction with dichloromethane. The organic layer was washed with brine, dried, filtered and concentrated in vacuo. This yielded 18.9 g of product which contained some dioxane.

TLC:=0.26, silica gel, dichloromethane/methanol 9/1 v/v.

N—Me-Boc-D-norLeu-Pro-OH.

First the N-succinimide ester was prepared starting from N—Me-Boc-D-norLeu-OH. 18 g of this derivative was dissolved in acetonitrile (250 ml), and then EDCI (14.5 g) and N-hydroxy-succinimide (HONSu) (8.7 g) were added. The reaction required 16 h at room temperature after which the solvent was removed, the residue was dissolved in ethyl acetate and washed with water and dried. This yielded 24.3 g of crude ONSu ester. The next step was to dissolve proline.HCl (20.9 g) in 300 ml dimethylformamide and 300 ml water and the pH was adjusted to 8 with 2N sodium hydroxide solution. A solution of the ONSu ester (24.3 g in 300 ml of dimethylformamide) was added dropwise to this solution keeping the pH constant. The reaction was completed after 5 h, after which the organic solvent was largely removed by evaporation under reduced pressure. Extra water (300 ml) was added and the pH was adjusted to 2. The product was extracted with ethyl acetate and washed with water. After drying, filtration and concentration the product was obtained as a yellow oil in 22.2 g. The crude product was chromatographed on silica using ethyl acetate/methanol 8/2 v/v as eluent. Yield: 13.2 g.

TLC: Rf=0.65, silica gel, ethyl acetate/pyridine/acetic acid/water=163/20/6/11 v/v/v/v.

N—Me—D-norLeu-Pro-Lys-(2-thiazolyl).

The mixed anhydride coupling between N—Me-Boc-D-norLeu-Pro-OH and H-Lys(Cbz)-(2-thiazolyl).TFA, the deprotection and the purification were done according to the procedures described in example 5. Yield: 107 mg.

Rt (LC): 23.22 min, 20% A, 80% B to 20% A, 20% B and 60% C in 40 min.

EXAMPLE 12

N—Me—D-Cha-Pro-Lys-(2-thiazolyl)

All steps leading to this tripeptide were performed in a similar manner as described for example 11, and starting with Boc-D-Cha-OH. Yield: 253 mg.

Rt (LC): 31.82 min, 20% A, 80% B to 20% A, 20% B and 60% C in 40 min.

EXAMPLE 13

N—Me—D-Phe-N-cyclopentyl-Gly-Lys-(2-thiazolyl)

N—Me-Boc-D-Phe-N-cyclopentyl-Gly-OMe

N—Me-Boc-D-Phe-OH (prepared according to example 11) (26 g) and N-cyclopentyl-Gly-OMe (21 g, see example 3) were dissolved in 300 ml of dimethylformamide. Next, TBTU (36 g) was added and the pH was adjusted to 8 with diisopropylethylamine (20 ml). The reaction mixture was stirred for 16 h and than concentrated in vacuo, dissolved in ethyl acetate, washed with sodium hydrogencarbonate (5%) and brine, dried on magnesium sulfate and again concentrated in vacuo. Yield: 24.8 g. TLC: Rf=0.62, silica gel, dichloromethane/methanol 95/5 v/v.

N—Me-Boc-D-Phe-N-cyclopentyl-Gly-OH

N—Me-Boc-D-Phe-N-cyclopentyl-Gly-OMe (17.3 g) was dissolved in 150 ml of tetrahydrofuran/water 135/15 v/v and 4 g of sodium hydroxide (in water) was added. After 2 h the reaction was stopped by adjusting the pH to 2 and the product was extracted with dichloromethane. After washing with water, drying on magnesium sulfate, concentrating in vacuo and crystallisation from dichloromethane/diethyl ether, the reaction yielded 13.1 g.

TLC: Rf=0.52, silica gel, dichloromethane/methanol 9/1 v/v.

N—Me-D-Phe-N-cyclopentyl-Gly-Lys-(2-thiazolyl)

The next steps were done according to the procedure described for example 11. Yield: 110 mg.

Rt (LC): 33.43 min, 20% A, 80% B to 20% A, 20% B and 60% C in 40 min.

EXAMPLE 14

N—Me-D-Phe-Pro-Lys-(2-thiazolyl)

N—Me-Boc-D-Phe-Pro-OH was prepared according to the description for example 1. The mixed anhydride coupling to H-Lys(Cbz)-(2-thiazolyl), the deprotection and the purification were done according to example 5. Yield: 148 mg.

Rt (LC): 27.22 min, 20% A, 80% B to 20% A, 20% B and 60% C in 40 min.

EXAMPLE 15

3,3-Diphenylpropionyl-Pro-Lys(ethoxycarbonyl)-(2-thiazolyl)

3,3-Diphenylpropionyl-Pro-Lys-(2-thiazolyl) was prepared as described in example 1. A solution was made of 20 mg of this dipeptide in dioxane/water 4/1 (4 ml) and the pH was adjusted with 1 N sodium hydroxide to 12. Next, 22 mg of ethylchloroformiate was added and the solution was stirred for 2 h at room temperature. The mixture was diluted with water and extracted with dichoromethane, washed with water, dried on magnesium sulfate, concentrated in vacuo and finally, freezedried from tert-butanol/water 1/1 v/v. Yield: 15 mg. TLC: Rf=0.92, silica gel, ethyl acetate/pyridine/acetic acid/water=63/20/6/11 v/v/v/v.

EXAMPLE 16

HOOC—$CH_2$—D-Cha-Pro-Lys-(2-oxazolyl)

Boc-Lys(Cbz)Ψ[CHOH]-(2-oxazolyl)

To a solution of 0.975 g of Boc-Lys(Cbz)-OMe in 25 ml of dichloromethane at −78° C. under a nitrogen atmosphere was added 6 ml of a 1M diisobutylaluminiumhydride solution in hexane. After 15 min the reaction was completed, the reaction mixture poured into 150 ml of 2% citric acid solution and filtered. The organic layer was separated, washed with water and brine, dried (magnesium sulfate) and concentrated. The residue was coevaporated with toluene to give 0.92 g of Boc-Lys(Cbz)-H. This aldehyde (0.89 g) was dissolved in 1.4 ml of toluene and 0.90 g of 2-(trimethylsilyl)oxazole (prepared according to: Edwards, P. D., Wolanin, D. J., Andisik D. W., and Davis W., J. Med. Chem. 38, 76 (1995)) was added and heated at 80° C. After 60 h the reaction mixture was concentrated, the residue dissolved in 5 ml of tetrahydrofuran, treated with 3 ml of a 3M tetrabutylammonium fluoride in tetrahydrofuran solution and stirred at room temperature for 2 h. The mixture was concentrated dissolved in ethyl acetate, washed with 3% aqueous sodium hydrogencarbonate solution and brine, dried (magnesium sulfate) and evaporated. Purification by column chromatography on silica gel eluting with a gradient of ethyl acetate/dichloromethane=2/1 (v/v) to ethyl acetate afforded an oil that was rechromatographed on silica gel eluting with a gradient of ethyl acetate/heptane=1/1 (v/v) to ethyl acetate/heptane=1/3 (v/v) to give 0.22 g of the title compound.

TLC: Rf=0.7, silica gel, ethyl acetate.

Boc-Lys(Cbz)-(2-oxazolyl)

To a solution of 0.22 g of Boc-Lys(Cbz)-Ψ[CHOH]—(2-oxazolyl) in 10 ml of dichloromethane was added 0.22 g of periodiane (Dess-Martin reagent). After 1.5 h stirring at room temperature 10 ml of aqueous 5% sodium thiosulfate was added and the mixture was stirred for 15 min at room temperature. The organic layer was separated, washed with water, aqueous 5% sodium hydrogen carbonate and brine, dried over magnesium sulfate and concentrated. Purification by chromatography on silica gel eluting with heptane/ethyl acetate=1/1 (v/v) yielded 162 mg of the title compound. TLC: Rf=0.5, silica gel, heptane/ethyl acetate=1/3 (v/v).

(tBuOOCCH$_2$)(Boc)-D-Cha-Pro-Lys(Cbz)-(2-oxazolyl)

The procedure described for example 5 was used. Deprotection of 0.16 g of Boc-Lys(Cbz)-(2-oxazolyl) and coupling with 0.19 g of (tBuOOCCH$_2$)(Boc)-D-Cha-Pro-OH afforded 0.19 g of (tBuOOCCH$_2$)(Boc)-D-Cha-Pro-Lys(Cbz)-(2-oxazolyl).

TLC: Rf=0.3, silica gel, heptane/ethyl acetate=1/3 (v/v).

HOOCCH$_2$—D-Cha-Pro-Lys-(2-oxazolyl)

The procedure described for example 5 was used. 0.19 g of (tBuOOCCH$_2$)(Boc)-D-Cha-Pro-Lys(Cbz)-(2-oxazolyl) afforded 52 mg of the title compound.

Rt (LC): 28.46 min, 20% A/80% B to 20% A/20% B/60% C in 40 min.

EXAMPLE 17

EthylSO$_2$-norLeu(cyclo)Gly-Lys-(2-thiazolyl)

Boc-L-α-amino-ε-caprolactam

To a stirred solution of L-α-amino-ε-caprolactam (10 g) in dioxane/water (2/1 v/v) (30 ml) was added 1N sodium hydroxide solution (7.8 ml) followed by di-t-butyl carbonate (18.8 g). The mixture was stirred for 16 h. at room temperature and concentrated in vacuo. The residue was dissolved in ethyl acetate and washed with water and brine, dried over sodium sulfate, filtered and evaporated in vacuo. The crude material was triturated by hexane, filtered and dried in vacuo to yield Boc-L-α-amino-ε-caprolactam (16 g).

TLC: Rf=0.85, ethyl acetate/heptane 1/1 v/v on silica.

Boc-norLeu(cyclo)Gly-OMe

Boc-L-α-amino-ε-caprolactam (10 g) was dissolved in dichloromethane (100 ml). At −20° C. a 1M solution of bis(trimethylsilyl)amide in THF/cyclohexane (1/1 v/v) (1 equiv.) was added slowly and the mixture was stirred for 30 min. Methyl bromoacetate (4 ml) was subsequently added and the mixture was stirred for 2 h. at room temperature. Additional bis(trimethylsilyl)amide in THF/cyclohexane (1/1 v/v) was added to force the reaction to completion. The mixture was diluted by dichloromethane and washed with 0.1 N hydrochloric acid solution, water, 5% aqueous sodium hydrogencarbonate solution and brine, dried over sodium sulfate, filtered and evaporated in vacuo. The residue was purified by chromatography on silica (eluent: heptane/ethyl acetate 6/4 v/v to yield Boc-norLeu(cyclo)Gly-OMe (12 g).

TLC: Rf=0.55, ethyl acetate/heptane 6/4 v/v on silica.

EthylSO$_2$-norLeu(cyclo)Gly-OMe

Boc-norLeu(cyclo)Gly-OMe (3 g) was dissolved in 50% TFA/dichloromethane (30 ml) and stirred for 1 h. at room temperature. The reaction mixture was evaporated in vacuo. The crude amine was dissolved in dichloromethane (30 ml) and a solution of ethanesulphonylchloride (1.29 g) in dichloromethane (10 ml) was added slowly at 0° C. Triethylamine was added to keep the pH at 8 during the reaction. The mixture was stirred for 1 h at room temperature, whereafter the mixture was concentrated in vacuo. The residue was dissolved in ethyl acetate and washed with 5% sodium hydrogencarbonate solution, water and brine, dried over sodium sulfate, filtered and evaporated in vacuo. The residue was purified by chromatography on silica (eluent: dichloromethane/ethyl acetate 95/5 v/v%. to yield ethylSO$_2$-norLeu(cyclo)Gly-OMe (1.45 g). TLC: Rf=0.30, dichloromethane/ethyl acetate 9/1 v/v on silica.

EthylSO$_2$-norLeu(cyclo)Gly-OH

A solution of ethylSO$_2$-norLeu(cyclo)Gly-OMe (1.45 g) in 50 ml of dioxane/water 9/1 v/v was treated with sufficient 1N sodium hydroxide to keep the pH at 13 for 2 hours at room temperature. After acidification, the mixture was poured into water and extracted with dichloromethane. The organic layer was washed with water and dried on sodium sulfate. The filtrate was evaporated and yielded 600 mg of the title compound.

TLC Rf=0.45, ethyl acetate/pyridine/acetic acid/water 63/20/6/11 v/v/v/v on silica.

EthylSO$_2$-norLeu(cyclo)Gly-Lys(Cbz)-(2-thiazolyl)

EthylSO$_2$-norLeu(cyclo)Gly-OH (482 mg) was dissolved in dry dimethylformamide (5 ml). After addition of ethyl diisopropyl amine (0.36 ml), the reaction mixture was placed under nitrogen and cooled to −20° C. Isobutylchloroformate (140 ml) was subsequently added and the mixture was allowed to stir for 15 min at −20° C. H-Lys(Cbz)-(2-thiazolyl).TFA was dissolved in dry dimethylformamide (3 ml) and added dropwise to the cold mixed anhydride solution, maintaining the pH at 8.5 by addition of ethyl diisopropyl amine. The reaction mixture was stirred for 15 min at −20° C. The reaction mixture was evaporated to dryness. The residue was dissolved in ethyl acetate and successively washed with 5% aqueous sodium hydrogencarbonate solution, water and brine, dried over sodium sulfate and concentrated in vacuo. The residue was purified by chromatography on silica (eluent: dichloromethane/methanol=95/5 v/v) to yield EthylSO$_2$-norLeu(cyclo)Gly-Lys(Cbz)-(2-thiazolyl)(607 mg).

TLC: Rf=0.63, ethyl acetate/pyridine/acetic acid/water 60/3/1/2 v/v/v/v on silica.

EthylSO$_2$-norLeu(cyclo)Gly-Lys-(2-thiazolyl)

EthylSO$_2$-norLeu(cyclo)Gly-Lys(Cbz)-(2-thiazolyl) (600 mg) was treated with trifluoroacetic acid/thioanisole 10/1 v/v (10 ml) for 4 h at room temperature. The reaction mixture was concentrated in vacuo and the residue was dissolved in water. The aqueous phase was washed extensively with diethyl ether. The water layer was concentrated in vacuo, coevaporated with diluted hydrochloric acid and lyophilised from water. The crude product was charged onto a preparative HPLC Deltapack C18 RP column using a gradient elution system of 200/4 A/80%B to 20% A/40% B/40% C over 40 minutes, at a flow rate of 50 ml/min. Yield: 233 mg of ethylSO$_2$-norLeu(cyclo)Gly-Lys-(2-thiazolyl).

R$_t$ (LC): 26.73 min. 20% A/80%B to 20% A/20% B/60% C in 40 minutes.

EXAMPLE 18

BenzylSO$_2$-norLeu(cyclo)Gly-Lys-(2-thiazolyl)

This compound was prepared in a similar manner as described in Example 17.

R$_t$ (LC): 37.05 min. 20% A/80%B to 20% A/20% B/60% C in 40 minutes.

EXAMPLE 19

7-Methoxy-2-Napthylsulphonyl-norLeu(cyclo)Gly-Lys-(2-thiazolyl)

This compound was prepared in a similar manner as described in Example 17.

$R_t$ (LC): 26.40 min. 20% A/60%B/20% C to 100% C in 40 minutes.

EXAMPLE 20

(4aR,8aR)-perhydroisoquinoline-1(R)-carbonyl-Pro-Lys-(2-thiazolyl)

2-Cbz-(4a,8aR)-perhydroisoquinoline-1(R,S)-carboxylic acid

2-Cbz-(4aR,8aR)-perhydroisoquinoline-1(R,S)-carboxylic acid has been synthesized as described in EP0643073, example 1.

TLC: Rf=0.85, ethyl acetate/pyridine/acetic acid/water 63/20/6/11 v/v/v/v on silica.

2-Cbz-(4aR,8aR)-perhydroisoquinoline-1(R,S)-carbonyl-Pr-O-tBu

To a cold solution (0° C.) of 2-Cbz-(4aR,8aR)-perhydroisoquinoline-1(R,S)-carboxylic acid (500 mg) in dimethylformamide (5 ml) were successively added DCCI (1,3-dicyclohexylcarbodiimide; 342 mg), HOBT (1-hydroxybenzotriazole hydrate; 319 mg), H-Pro-OtBu (270 mg) and triethylamine (0.55 ml). The reaction mixture was stirred at 0° C. for 1 h. and then kept at room temperature overnight. The reaction mixture was cooled to −20° C. and the DCU (1,3-dicyclohexylurea) was removed by filtration. The filtrate was concentrated in vacuo and the residue was dissolved in ethyl acetate. This solution was washed successively with 5% aqueous sodium hydrogencarbonate solution, 3% aqueous citric acid solution, water and brine, dried over sodium sulfate and concentrated in vacuo. The residue was purified by chromatography on silica (eluent: heptane/ethyl acetate 4/1 v/v) to yield 2-Cbz-(4aR,8aR)-perhydroisoquinoline-1(R,S)-carbonyl-Pro-O-tBu) (634 mg).

TLC: Rf=0.90, ethyl acetate/pyridinelacetic acid/water 63/20/6/11 v/v/v/v on silica.

2-Cbz-(4aR,8aR)-perhydroisoquinoline-1(R,S)-carbonyl-Pro-OH

2-Cbz-(4aR,8aR)-perhydroisoquinoline-1(R,S)carbonyl-Pro-O-t-butyl ester (600 mg) was stirred in a mixture of dichloromethane (1 ml), trifluoroacetic acid (3 ml), anisole (0.15 ml) for 1 h at room temperature. The reaction mixture was concentrated in vacuo at low temperature and the residue was dissolved in water at pH 9.5. The aqueous phase was washed with diethyl ether, whereafter the aqueous layer was acidified to pH 2.5 by 2M hydrochloric acid solution. The aqueous layer was extracted with ethyl acetate and the organic phase was washed with brine, dried over sodium sulfate and concentrated in vacuo to yield 2-Cbz-(4aR,8aR)-perhydroisoquinoline-1(R,S)-carbonyl-Pro-OH (588 mg). TLC: Rf=0.54, ethyl acetate/pyridine/acetic acid/water 60/3/1/2 v/v/v/v on silica.

2-Cbz-(4aR,8aR)-perhydroisoquinoline-1(R,S)-carbonyl-Pro-Lys(Cbz)-(2-thiazolyl)

2-Cbz-(4aR,8aR)-perhydroisoquinoline-1(R,S)-carbonyl-Pro-OH (500 mg) was dissolved in dry dimethylformamide (5 ml). After addition of ethyl diisopropyl amine (0.41 ml), the reaction mixture was placed under nitrogen and cooled to −20° C. Isobutylchloroformate (156 ml) was subsequently added and the mixture was allowed to stir for 15 min at −20° C. H-Lys(Cbz)-(2-thiazolyl).TFA (594 mg) was dissolved in dry dimethylformamide (3 ml) and added dropwise to the cold mixed anhydride solution, maintaining the pH 8.5 by addition of ethyl diisopropyl amine. The reaction mixture was stirred for 15 min at −20° C. The reaction mixture was evaporated to dryness. The residue was dissolved in ethyl acetate and successively washed with 5% aqueous sodium hydrogencarbonate solution, water and brine, dried over sodium sulfate and concentrated in vacuo. The residue was purified by chromatography on silica (eluent: dichloromethane/methanol=95/5 v/v %) to yield 2-Cbz-(4aR,8aR)-perhydroisoquinoline-1(R,S)-carbonyl-Pro-Lys (Cbz)-(2-thiazolyl)(880 mg). TLC: Rf=0.42, ethyl acetate/heptane 3/1 v/v on silica.

(4aR,8aR)-perhydroisoquinoline-1(R,S)-carbonyl-Pro-Lys-(2-thiazolyl)

(4aR,8aR)-perhydroisoquinoline-1(R,S)-carbonyl-Pro-Lys-(2-thiazolyl) (875 mg) was treated with trifluoroacetic acid/thioanisole 10/1 v/v (10 ml) for 4 h at room temperature. The reaction mixture was concentrated in vacuo and the residue was dissolved in water. The aqueous phase was washed extensively with diethyl ether. The water layer was concentrated in vacuo, coevaporated with diluted hydrochloric acid and lyophilised from water. The crude product was charged onto a preparative HPLC Deltapack C18 RP column using a gradient elution system of 20% A/80%B to 20% A/53% B/27% C over 40 minutes, at a flow rate of 50 ml/min. Yield: 211 mg of (4aR,8aR)-perhydroisoquinoline-1(R)-carbonyl-Pro-Lys-(2-thiazolyl).

$R_t$ (LC): 28 min. 20% A/80%B to 20% A/20% B/60% C in 40 minutes.

EXAMPLE 21

EthylSO$_2$—D-Cha-Pro-Lys-(2-thiazolyl)

Boc-D-Cha-Pro-OBzl (Bzl=benzyl)

Boc-D-Cha-Pro-OBzl was prepared according a similar manner as described in example 1 using Boc-D-Cha and Pro-OBzl.

TLC: Rf=0.5, dichloromethane/methanol 95/5 v/v on silica.

EthylSO$_2$—D-Cha-Pro-OBzl

Boc-D-Cha-Pro-OBzl (3.8 g) was dissolved in 50% TFA/dichloromethane (25 ml) and stirred for 30 minutes at room temperature. The reaction mixture was evaporated in vacuo. The crude amine was dissolved in dichloromethane (50 ml) and ethanesulphonylchloride (0.8 ml) was added at −78° C. Triethylamine was added to keep the pH 8 during the reaction. The mixture was stirred for 3 h at 0° C., whereafter water (25 ml) was added. After an additional stirring for 30 minutes at room temperature, the reaction mixture was concentrated in vacuo. The residue was dissolved in diethyl ether and washed with 1N hydrochloric acid solution, water, 5% sodium hydrogencarbonate solution and brine, dried over sodium sulfate, filtered and evaporated in vacuo. Trituration of the crude material with methanol yielded ethylSO$_2$—D-Cha-Pro-OBzl (3.0 g). TLC: Rf=0.6, dichloromethane/methanol 95/5 v/v on silica.

EthylSO$_2$—D-Cha-Pro-OH

To a solution of EthylSO$_2$—D-Cha-Pro-OBzl (10 g) in tetrahydrofuran (250 ml) was added 1M solution of tetrabutylammonium fluoride in tetrahydrofuran (84 ml). The reaction mixture was stirred for 30 minutes at room temperature and poured into water (11). The aqueous solution was extracted with ethyl acetate. The combined organic layers were successively washed with 1N hydrochloric acid solution and water, dried over sodium sulfate and concentrated in vacuo. The residue was purified by crystallisation from ethyl acetate/diisopropylether to yield EthylSO$_2$—D-Cha-Pro-OH (6.0 g).

TLC: Rf=0.2, ethyl acetate/pyridinelacetic acid/water 163/20/6/11 v/v/v/v on silica.

EthylSO$_2$—D-Cha-Pro-Lys(Cbz)(2-thiazolyl)

EthylSO$_2$—Dha-Pro-OH (397 mg) was dissolved in dry dimethylformamide (3 ml). After addition of ethyl diisopropyl amine (0.19 ml), the reaction mixture was placed under nitrogen and cooled to −20° C. Isobutylchloroformate (130 ml) was subsequently added and the mixture was allowed to stir for 15 min at −20° C. H-Lys(Cbz)42-thiazolyl).TFA was dissolved in dry dimethylformamide (3 ml) and added dropwise to the cold mixed anhydride solution, maintaining the pH at 8.5 by addition of ethyl diisopropyl amine. The reaction mixture was stirred for 15 min at −20° C. and 1 h at room temperature. The reaction mixture was evaporated to dryness. The residue was dissolved in ethyl acetate and successively washed with 5% aqueous sodium hydrogen-carbonate solution, water and brine, dried over sodium sulfate and concentrated in vacuo. The residue was purified by chromatography on silica (eluent: ethyl acetate/heptane 2/1 v/v) to yield EthylSO$_2$—D-Cha-Pro-Lys(Cbz)-(2-thiazolyl)(575 mg).

TLC: Rf=0.32, ethyl acetate/heptane 2/1 v/v on silica.

EthylSO$_2$—D-Cha-Pro-Lys-(2-thiazolyl)

EthylSO$_2$—D-Cha-Pro-Lys(Cbz)-(2-thiazolyl) (570 mg) was treated with trifluoroacetic acid/thioanisole 10/1 v/v (44 ml) for 4 h at room temperature. The reaction mixture was concentrated in vacuo and the residue was dissolved in water. The aqueous phase was washed extensively with diethyl ether. The water layer was concentrated in vacuo, coevaporated with diluted hydrochloric acid and lyophilised from water. The crude product was charged onto a preparative HPLC Deltapack C18 RP column using a gradient elution system of 20% A/80%B to 20% A/30% B/50% C over 40 minutes, at a flow rate of 80 ml/min. Yield: 275 mg of EthylSO$_2$—D-Cha-Pro-Lys-(2-thiazolyl).

R$_t$ (LC): 26.06 min. 20% A/60%B/20% C to 100% C in 40 minutes.

EXAMPLE 22

EthylSO$_2$—D-Phe-Pro-Lys-(2-thiazolyl)

Boc-D-Phe-Pro-OBzl

This compound was prepared according a similar manner as described in example 1 using Boc-D-Phe and Pro-OBzl.

TLC: Rf=0.9, ethyl acetate/pyridine/acetic acid/water 60/3/1/2 v/v/v/v on silica EthylSO$_2$—D-Phe-Pro-OH This compound was prepared according a similar manner as described in example 21 using Boc-D-Phe-Pro-OBzl.

TLC: Rf=0.48, ethyl acetate/pyridine/acetic acid/water 163/20/6/11 v/v/v/v on silica.

EthylSO$_2$—D-Phe-Pro-Lys(Cbz)-(2-thiazolyl)

EthylSO$_2$—D-Phe-Pro-Lys(Cbz)2-thiazolyl) was prepared according a similar manner as described in example 21 using EthylSO$_2$—D-Phe-Pro-OH and Lys(Cbz)2-thiazolyl).

TLC: Rf=0.32, ethyl acetate/heptane 8/2 v/v on silica

EthylSO$_2$—D-Phe-Pro-Lys-(2-thiazolyl).

EthylSO$_2$—D-Phe-Pro-Lys(Cbz)-(2-thiazolyl) (336 mg) was treated with trifluoroacetic acid/thioanisole 10/1 v/V (44 ml) for 4 h at room temperature. The reaction mixture was concentrated in vacuo and the residue was dissolved in water. The aqueous phase was washed extensively with diethyl ether. The water layer was concentrated in vacuo, coevaporated with diluted hydrochloric acid and lyophilised from water. The crude product was charged onto a preparative HPLC Deltapack C18 RP column using a gradient elution system of 20% A/65%B/ 15% C to 20% A/20% B/60% C over 40 minutes, at a flow rate of 50 ml/min). Yield: 160 mg of EthylSO$_2$—D-Phe-Pro-Lys-(2-thiazolyl).

R$_t$ (LC): 39.47 min. 20% A/80% B to 20% A/20% B/60% C in 40 minutes.

EXAMPLE 23

D-Hpl-Pro-Lysz(2-thiazolyl) (Hpl=3-hexahydrophenyl lactic acid)

H—D-Hpl-OMe

H—D-Cha-OH (1.0 g) was dissolved in a mixture of 1N hydrochloric acid (4.8 ml), water (19.4 ml) and acetic acid (9.7 ml). At 0° C. a solution of sodium nitrite (3.4 g) in water (5.8 ml) was added slowly and the mixture was stirred overnight at room temperature. Hydrochloric acid, 37%, (4.8 ml) was subsequently added and the mixture was stirred for 15 min at room temperature. The reaction mixture was evaporated and the residue was dissolved in ether/acetone. After filtration, the solution was concentrated in vacuo and the crude material was stirred in methanol (25 ml) for 18 h. The pH was 1.5. The reaction mixture was evaporated to dryness and the residue was purified by chromatography on silica (eluent: toluene/methanol 97/3 v/v. to yield H—D-Hpl-OMe (612 mg)

TLC: Rf=0.9, ethyl acetate/pyridine/acetic acid/water 163/20/6/11 v/v/v/v on silica.

THP-D-Hpl-OMe (THP=tetrahydropyran)

To a stirred solution of H—D-Hpl-OMe(450 mg) in dichloromethane (2 ml) was successively added 3,4-dihydro-2H-pyran (0.285 ml) and pyridinium p-toluenesulfonate (60 mg). The mixture was stirred for 6 h. at room temperature and diluted with ether. This mixture was washed with brine, dried over sodium sulfate, filtered and evaporated in vacuo. The crude material was purified by chromatography on silica (eluent: ethyl acetate/heptane 1/4 v/v) to yield THP-D-Hpl-OMe (498 mg).

TLC: Rf=0.64, ethyl acetate/heptane 1/2 v/v on silica.

THP-D-Hpl-OH

A solution of THP-D-Hpl-OMe (10.3 g) in of dioxane/water 9/1 (200 ml) was treated with sufficient 1N sodium hydroxide to keep the pH at 12 for 18 hours at room temperature. After acidification, the mixture was poured into water (500 ml) and extracted with dichloromethane. The organic layer was washed with water and dried on sodium sulfate The filtrate was evaporated and yielded 6.6 g of the title compound.

TLC: Rf=0.78, ethyl acetate/pyridine/acetic acid/water 163/20/6/11 v/v/v/v on silica.

THP-D-Hpl-Pro-OH

To a solution of THP-D-Hpl-OH (5.87 g) in acetonitrile (75 ml). was successively added EDCI (1-(3- dimethylaminopropyl)-3-ethylcarbodiimide hydrochloride) (4.84 g) and N-hydroxysuccinimide (2.9 g). The reaction mixture was stirred at room temperature for 16 h. The mixture was concentrated in vacuo and the residue was dissolved in ethyl acetate. This solution was washed with water and brine, dried over sodium sulfate and concentrated in vacuo. The crude material was dissolved in dimethylformamide (100 ml) and added to a solution of proline.HCl (6.99 g) in dimethylformamide/water, 1/1, v/v (200 ml), which was adjusted to a pH of 8.5 by sodium hydroxide. After stirring overnight the reaction mixture was concentrated in vacuo and the residue was dissolved in water. This aqueous solution was adjusted to pH 2.5 at 0° C., followed by extraction with ethyl acetate. The combined organic layers were successively washed with water and brine, dried over sodium sulfate and concentrated in vacuo. The crude material was purified by chromatography on silica (eluent: ethyl acetate/methanol, 8/2 6/4, v/v %) to yield THP-D-Hpl-Pro-OH (6.75 g).

TLC: Rf=0.52, ethyl acetate/pyridine/acetic acid/water 163/20/6/11 v/v/v/v on silica.

THP-D-Hpl-Pro-Lys(Cbz)-(2-thiazolyl)

THP-D-Hpl-Pro-OH (390 mg) was dissolved in dry dimethylformamide (5 ml). After addition of ethyl diisopropyl amine (0.19 ml), the reaction mixture was placed under nitrogen and cooled to −20° C. Isobutylchloroformate (130 ml) was subsequently added and the mixture was allowed to stir for 15 min at −20° C. H-Lys(Cbz)-(2-thiazolyl).TFA (1.05 eq.) was dissolved in dry dimethylformamide (5 ml) and added dropwise to the cold mixed anhydride solution, maintaining the pH at 8.5 by addition of ethyl diisopropyl amine. The reaction mixture was stirred for 15 min at −20° C. and 2.5 h. at room temperature. The reaction mixture was evaporated to dryness. The residue was dissolved in ethyl acetate and successively washed with 5% aqueous sodium hydrogencarbonate solution, water and brine, dried over sodium sulfate and concentrated in vacuo. The residue was purified by chromatography on silica (eluent: ethyl acetate/heptane 2/1 v/v) to yield THP-D-Hpl-Pro-Lys(Cbz)-(2-thiazolyl) (497 mg).

TLC: Rf=0.42 in ethyl acetate/heptane 2/1 v/v on silica.

D-Hpl-Pro-Lys-(2-thiazolyl)

THP-D-Hpl-Pro-Lys(Cbz)-(2-thiazolyl) (470 mg) was treated with trifluoroacetic acid/thioanisole 10/1 v/v (38.5 ml) for 4 h at room temperature. The reaction mixture was concentrated in vacuo and the residue was dissolved in water. The aqueous phase was washed extensively with diethyl ether. The water layer was concentrated in vacuo, coevaporated with diluted hydrochloric acid and lyophilised from water. The crude product was charged onto a preparative HPLC Deltapack C18 RP column using a gradient elution system of 20% A/65%B/15% C to 20% A/20% B/60% C over 40 minutes, at a flow rate of 50 ml/min. Yield: 75 mg of D-Hpl-Pro-Lys-(2-thiazolyl).

R$_t$ (LC): 40.00 min. 20% A/80% B to 20% A/20% B/60% C in 40 minutes.

EXAMPLE 24

HOOC—CH$_2$—D-Phe-Pro-Lys-(2-thiazolyl)

HLD-Phe-OMe.HCl

To cold (−20° C.) and dry methanol (1 l) was added dropwise thionylchloride (130 ml). H—D-Phe-OH.HCl (147.6 g) was added and the reaction mixture was heated under reflux for 30 min and then kept at room temperature overnight. The mixture was concentrated in vacuo and coevaporated with methanol (3 times). The residue was crystallized from methano/diethyl ether yielding H—D-Phe-OMe.HCl as a white crystalline powder (187.4 g). TLC: R$_f$=0.54, silica gel, n-butanolacetic acid/water 10/1/3 v/v.

N-(t-Butyloxycarbonylmethyl)-D-Phe-OMe t-Butyl-bromo acetate (65 ml) was added to a stirred solution H—D-Phe-OMe.HCl (65.2 g) in 400 ml of acetonitrile. The pH of the mixture was adjusted to 8.5 with N,N-diisopropylethylamine. The mixture was stirred for 16 hours at room temperature and evaporated in vacuo. The residue was dissolved in dichloromethane and the solution was washed with water, dried on sodium sulfate and evaporated in vacuo. Chromatography over silica gel in heptane/ethyl acetate 9/1 (v/v) gave 96.4 g of N-(t-butyloxycarbonylmethyl)-D-Phe-OMe. TLC: R$_f$=0.90, silica gel, ethyl acetate/pyridine/acetic acid/water 376/31/18/7 v/v/v/v.

N-(t-Butyloxycarbonylmethyl)—N-Boc-D-Phe-OMe

The pH of a solution of N-(t-butyloxycarbonylmethyl)-D-Phe-OMe (96.4 g) and di-t-butyl dicarbonate (72.2 g) in N,N-dimethyl formamide (400 ml) was adjusted to 8.5 with N,N-diisopropylethylamine. The mixture was stirred for 48 h at room temperature. The solvent was removed in vacuo. Dichloromethane and water were added to the residue. The organic layer was separated, washed with cold 1N hydrogen chloride, water, saturated sodium hydrogen carbonate solution and water. The organic layer was dried over sodium sulfate and the filtrate was evaporated. The residue was chromatographed on silica in toluene/ethyl acetate 9/1 (v/v) as eluent. The fractions containing N-(t-Butyloxycarbonylmethyl)-N-Boc-D-Phe-OMe were pooled and evaporated. Yield: 115.3 g. TLC: R$_f$=0.77, silica gel, toluene/ethyl acetate 9/1 v/v.

N-(t-Butyloxycarbonylmethyl)—N-Boc-D-Phe-OH

A solution of N-(t-butyloxycarbonylmethyl)-N-Boc-D-Phe-OMe (115.3 g) in 800 ml of dioxane/water=9/1 (ylv) was treated with sufficient 2N sodium hydroxide to keep the pH at 12 for 16 hours at room temperature. After acidification, the mixture was poured into water stand was extracted with dichloromethane. The organic layer was washed with water and was dried over sodium sulfate. The filtrate was evaporated and yielded 104 g of N-(t-butyloxycarbonylmethyl)-N-Boc-D-Phe-OH.

TLC: R$_f$=0.10, silica gel, toluene/ethyl acetate 7/3 v/v.

N-(t-Butyloxycarbonylmethyl)-N-Boc-D-Phe-Pro-OBzl

To a cold (0° C.) solution of N-(t-butyloxycarbonylmethyl)-N-Boc-D-Phe-OH (5.3 g) in N,N-dimethyl formamide (40 ml) were successively added 1-hydroxy benzotriazole (2.8 g), dicyclohexyl carbodiimide (3.2 g), H-Pro-OBzl.HCl (3.78 g) and triethylamine (2.16 ml). The mixture was stirred at 0° C. for 1 hour and then kept at room temperature overnight. The mixture was cooled to −20° C. and dicyclohexylurea was removed by filtration. The filtrate was evaporated to dryness. The residue was dissolved in ethyl acetate and washed successively with 5% sodium hydrogen carbonate, water, 2% citric acid and brine, dried over sodium sulfate and concentrated in vacuo. The residue was chromatographed on silica gel in heptane/ethyl acetate 6/4 (v/v) as eluent. The fractions containing N-(t-butyloxycarbonylmethyl)-N-Boc-D-Phe-Pro-OBzl were pooled and evaporated. Yield: 4.35 g. TLC: $R_f$=0.74, silica gel, heptane/ethyl acetate 1/1 v/v.

N-(t-Butyloxycarbonylmethyl)-N-Boc-D-Phe-Pro-OH

10% palladium on charcoal (450 mg) was added to a solution of N-(t-Butyloxy-carbonylmethyl)-N-Boc-D-Phe-Pro-OBzl (4.35 g) in methanol (50 ml). The mixture was hydrogenated at atmospheric pressure at room temperature for 45 min. The palladium catalyst was removed by filtration and the solvent was removed by evaporation at reduced pressure yielding 3.48 g N-(t-Butyloxycarbonylmethyl)-N-Boc-D-Phe-OH.

TLC: $R_f$=0.63, silica gel, ethyl acetate/pyridine/acetic acid/water 664/31/18/7 v/v/v/v.

N-(t-Butyloxycarbonylmethyl)-N-Boc-D-Phe-Pro-Lys(Cbzh(2-thiazolyl)

To a cooled (−20° C.) solution of 375 mg N-(t-butyloxycarbonylmethyl)-N-Boc-D-Phe-Pro-OH and 276 ml N,N-diisopropylethylamine in 10 ml of N,N-dimethyl formamide, 100 ml isobutyl chloroformate was added. The reaction mixture was stirred for another 20 minutes at −20° C. H-Lys(Cbz)-(2-thiazolyl).TFA (362 mg) was dissolved in 5 ml N,N-dimethyl formamide and adjusted to pH 8 with N,N-diisopropylethylamine. This solution was slowly added to the reaction mixture. The reaction mixture was stirred for 15 min at −20° C. and then allowed to warm up to room temperature. The reaction mixture was evaporated to dryness and the residue was dissolved in ethyl acetate. The organic phase was washed with 5% sodium hydrogencarbonate, water and brine, dried over sodium sulfate and concentrated to give 622 mg of crude product. Silica gel purification, using dichloromethane/methanol 97/3 v/v as eluent, afforded 394 mg of N-(t-butyloxycarbonylmethyl)-N-Boc-D-Phe-Pro-Lys(Cbz)-(2-thiazolyl). TLC: $R_f$=0.50, silica gel, dichloromethane/methanol 95/5 v/v.

HOOC—CH$_2$—D-Phe-Pro-Lys-(2-thiazolyl)

The protected tripeptide (394 mg) was treated with trifluoroacetic acid and thioanisole according to the procedures described in example 1 to afford, after HPLC purification, 206 mg of HOOC—CH$_2$—D-Phe-Pro-Lys2-thiazolyl).

$R_t$ (C); 27.9 min, 20% A, 80% B to 20a A, 20% B and 60% C in 40 min.

EXAMPLE 25

HOOC-CH$_2$—D-p-OCH$_3$-Phe-Pro-Lys-(2-thiazolyl)

HOOC—CH$_2$—D-p-OCH$_3$-Phe-Pro-Lys-(2-thiazolyl) was prepared in a similar manner as described in example 24, starting from H—D-p-OCH$_3$-Phe-OH. HCl. Deprotection (see example 1) of 345 mg N-(t-butyloxycarbonylmethyl)-N-Boc-D-p-OCH$_3$-Phe-Pro-Lys (Cbz)-(2-thiazolyl) gave, after HPLC purification, 153 mg of the product.

$R_t$ (LC): 28.9 min, 20% A, 80% B to 20% A, 20% B and 60% C in 40 min.

EXAMPLE 26

HOOC—CH$_2$—D/L-m-F-Phe-Pro-Lys-(2-thiazolyl)

N-(t-Butyloxycarbonylmethyl)-N-Boc-D/L-m-F-Phe-OH

According to analogous procedures as described in example 24, H—DAL-m-F-Phe-OH. HCl (5 g) was converted into N-(t-butyloxycarbonylmethyl)-N-Boc-D/L-m-F-Phe-OH. Yield: 8 g. TLC: $R_f$=0.65, silica gel, ethyl acetate/methanol 9/1 v/v.

N-(t-Butyloxycarbonylmethyl)-N-Boc-D/L-m-F-Phe-Pro-OMe

To a cold (0° C.) solution of N-(t-butyloxycarbonylmethyl)-N-Boc-D/L-m-F-Phe-OH (7.9 g) in N,N-dimethyl formamide (80 ml) were successively added 1-hydroxy benzotriazole (4.0 g), dicyclohexyl carbodiimide (4.5 g), H-Pro-OMe.HCl (3.6 g) and triethylamine (3.25 ml). The mixture was stirred at 20° C. for 1 hour and then kept at room temperature overnight. The mixture was cooled to −20° C. and dicyclohexylurea was removed by filtration. The filtrate was evaporated to dryness. The residue was dissolved in ethyl acetate and washed successively with 5% sodium hydrogencarbonate, water, 2% citric acid and brine, dried over sodium sulfate and concentrated in vacuo. The residue was purified over silica gel in heptane/ethyl acetate 7/3 v/v, to afford 6.9 g of the product. TLC: $R_f$=0.65 heptane/ethyl acetate 1/1, v/v.

N-(t-Butyloxycarbonylmethyl)-N-Boc-D/L-m-F-Phe-Pro-OH 6.9 g of N-(t-Butyloxycarbonylmethyl)-N-Boc-D/L-m-F-Phe-Pro-OMe, dissolved in dioxane/water: 9/1 v/v (60 ml), was treated with a 1 N sodium hydroxide solution (13.8 ml) portionwise over 16 hours, keeping the pH at 10–10.5. The reaction mixture was diluted with ice-water and acidified with 2 N hydrogen chloride solution until pH 2. The aqueous layer was extracted with dichloromethane. Next, the organic phase was washed with cold water, dried over sodium sulfate and concentrated to give 14.7 g crude material. Purification over silica gel in ethyl acetate/methanol 9/1 v/v afforded 5.22 g. TLC: $R_f$=0.20, silica gel, ethyl acetate/methanol 8/2 v/v.

N-(t-Butyloxycarbonylmethyl)-N-Boc-D/L-m-F-Phe-Pro-Lys(Cbz)-(2-thiazolyl)

Coupling of N-(t-butyloxycarbonylmethyl)-N-Boc-D/L-m-F-Phe-OH (601.3 mg) with H-Lys(Cbz)-(2-thiazolyl) was performed under the same conditions as described in example 24. Yield: 684.3 mg. TLC: $R_f$=0.74, silica gel, dichloromethane/methanol 95/5 v/v.

HOOC—CH$_2$—D/L-m-F-Phe-Pro-Lys-(2-thiazolyl)

N-(t-butyloxycarbonylmethyl)-N-Boc-D/L-m-F-Phe-Pro-Lys(Cbz)-(2-thiazolyl) (673.5 mg) was treated under the same conditions with trifluoroacetic acid and thioanisole as described in example 1 to afford 259 mg of pure product after HPLC-purification.

$R_t$ (LC): 28.4 min and 29.0 min, 20% A, 80% B to 20% A, 20% B and 60% C in 40 min.

EXAMPLE 27

HOOC—CH$_2$—D-p-CF$_3$-Phe-Pro-Lys-(2-thiazolyl)

N-(t-Butyloxycarbonylmethyl)N-Boc-D/L-p-CF$_3$-Phe-OH

According to analogous procedures as described in example 24, H—D/L-p-CF$_3$-Phe-OH. HCl (10.12 g) was converted into N-(t-Butyloxycarbonylmethyl)-N-Boc-D/L-p-CF$_3$-Phe-OH. Yield: 12.23 g. TLC: $R_f$=0.64, silica gel, ethyl acetate/methanol 9/1, v/v.

N-(1-Butylo yaronylmetbyM)-N-Boc-D-p-CF₃-Phe-Pro-OBzl

An amount of 6.10 g N-(t-Butyloxycarbonylmethyl)-N-Boc-D/L-p-CF3-Phe-OH was coupled to H-Pro-OBzl. HCl according to the same procedure as described in example 24. After work-up, the diastereoisomers could be separated by silica gel, using heptane/ethyl acetate 75/25 v/v, to afford 0.63 g of pure N-(t-Butyloxycarbonylmethyl)-N-Boc-D-p-CF₃-Phe-Pro-OBzl.

TLC: $R_f$=0.35, silica gel, heptane/ethyl acetate 7/3 ylv.

N-(t-butyloxocarbonylmethyl)-N-Boc-D-p-CF₃-Phe-Pro-Lys(Cbz)-(2-thiazolyl)

N-(t-butyloxycarbonylmethyl)-N-Boc-D-p-CF₃-Phe-Pro-OBzl (630 mg) was reduced and subsequently coupled to H-Lys(Cbz)-(2-thiazolyl) using the procedures as described in example 24. Yield: 317.7 mg. TLC: $R_f$=0.46, dichloromethane/methanol 95/5 v/v.

HOOC—CH₂—D-p-CF₃-Phe-Pro-Lys-(2-thiazolyl)

The removal of the protected groups from N-(t-butyloxycarbonylmethyl)N-Boc-D-p-CF₃-Phe-Pro-Lys(Cbz)-(2-thiazolyl) (306.5 mg) was performed using the same method as described in example 24. After HPLC purification 157 mg of product was isolated.

$R_t$ (LC)=36.7 min, 20% A, 80% B to 20% A, 20% B and 60% C in 40 min.

EXAMPLE 28

HOOC—CH₂—D-p-Cl-Phe-Pro-Lys-(2-thiazolyl)

N-(t-Butyloxycarbonylmethyl)-N-Boc-D-p-Cl-Phe-OH

According to analogous procedures as described in example 24, H—D-p-Cl-Phe-OH. HCl (10 g) was converted into N-(t-Butyloxycarbonylmethyl)-N-Boc-D-p-Cl-Phe-OH. Yield: 16.7 g. TLC: $R_f$=0.27, silica gel, ethyl acetate/methanol 9/1, v/v.

N-(t-butyloxycarbonylmethyl)-N-Boc-D-p-Cl-Phe-ONSu

A solution of N-(t-butyloxycarbonylmethyl)-N-Boc-D-p-Cl-Phe-OH (14.67 g) in 250 ml acetonitrile was treated with N-hydroxysuccinimide (4.11 g) and 1-(3-dimethylaminopropyl)3-ethylcarbodiimide (EDCI) hydrochloride (6.86 g) overnight at room temperature. The reaction mixture was evaporated to dryness and the residue was dissolved in ethyl acetate. The organic phase was washed with water, dried over sodium sulfate and concentrated to afford 19.11 g active ester, which was directly used in the next step.

N-(t-butyloxycarbonylmethyl)-N-Boc-D-p-Cl-Phe-Pro-OH

H-Pro-OH.HCl (10.79 g) was dissolved in 100 ml N,N-dimethyl formamide and 100 ml water. The pH of the reaction mixture was adjusted to 8 with a 1 N sodium hydroxide solution, whereafter N-(t-butyloxycarbonylmethyl)-N-Boc-D-p-Cl-Phe-ONSu (19.11 g), dissolved in 120 ml of N,N-dimethyl formamide, was added dropwise. The reaction was stirred overnight at room temperature at pH 8. The reaction mixture was cooled and adjusted to pH 2 with 1 N hydrochloric acid. The aqueous layer was extracted with dichloromethane. The organic phase was washed with water, dried over sodium sulfate en evaporated in vacuo. Silica gel purification, using a gradient ethyl acetate/methanol 9/1 TLC: $R_f$=0.24, silica gel, ethyl acetate/methanol 8/2 v/v.

N-(t-butyloxycarbonylmethyl)-N-Boc-D-p-Cl-Phe-Pro-Lys(Cbz)-(2-thiazolyl)

According to the procedures described in example 24, N-(t-butyloxycarbonylmethyl)-N-Boc-D-p-Cl-Phe-OH (369.4 mg) was converted into the target compound. Yield: 249.1 mg.

TLC: $R_f$=0.25, silica gel, dichloromethane/methanol 97/3 v/v.

HOOC—CH₂—D-p-Cl-Phe-Pro-Lys-(2-thiazolyl)

As described in example 1, 231.5 mg N-(t-butyloxycarbonylmethyl)-N-Boc-D-p-Cl-Phe-Pro-Lys(Cbz)(2-thiazolyl) was deprotected and purified to obtain 109.8 mg of the product.

$R_t$ (LC)=33.8 min, 20% A, 80% B to 20% A, 20% B and 60% C in 40 min.

EXAMPLE 29

HOOC—CH₂—D-o-Cl-Phe-Pro-Lys-(2-thiazolyl)

HOOC—CH₂—D-o-Cl-Phe-Pro-Lys-(2-thiazolyl) was prepared in a similar manner as described in example 26, starting from H—D/L-o-Cl-Phe-OH.HCl. The two diastereoisomers were separated in the protected tripeptide stage. Deprotection of 230 mg of N-(t-butyloxycarbonylmethyl)N-Boc-D-o-Cl-Phe-Pro-Lys(Cbz)-(2-thiazolyl), according to the method described in example 1, afforded 116 mg product after HPLC purification.

$R_t$ (LC)=30.0 min, 20% A, 80% B to 20% A, 20% B and 60% C in 40 min.

EXAMPLE 30

HOOC—CH—D/L-m,p-di-F-Phe-Pro-Lys-(2-thiazolyl)

This compound was prepared in a similar manner as described in example 26, starting from H—D/L-m,p-di-F-Phe-OH.HCl. Removal of the blocking groups of the protected tripeptide (720 mg) followed by HPLC purification, as described in example 1, afforded 170 mg of the product.

$R_t$ (LC)=30.7 min and 31.1 min, 20% A, 80% B to 20% A, 20% B and 60% C in 40 min.

EXAMPLE 31

HOOC—CH₂—D/L-o,p-di-Cl-Phe-Pro-Lys-(2-thiazolyl)

This compound was prepared in a similar manner as described in example 26, starting from H—D/L-o,p-di-aPhe-OH.HCl. Removal of the blocking groups of the protected tripeptide (1.07 g) followed by HPLC purification, as described in example 1, afforded 100 mg of the product.

$R_t$ (LC)=35.4 min and 36.1 min, 20% A, 80% B to 20% A, 20% B and 60% C in 40 min.

EXAMPLE 32

HOOC—CH₂—D-Tyr-Pro-Lys-(2-thiazolyl)

Cbz-D-Tyr(tBu)-OH

N-benzyloxycarbonyloxysuccinimide (5.75 g) was added to a suspension of D-Tyr(tBu)-OH (5.0 g) in N,N-dimethyl formamide (40 ml). The pH of the solution was adjusted to 8 using triethylamine. The reaction mixture was stirred overnight at room temperature and then evaporated to dryness in vacuo. The residue was dissolved in dichloromethane and diluted with ice water. The pH of the water layer was adjusted to pH 2.5 with 2 N hydrogen chloride. The organic layer was seperated and the aqueous phase was extracted with dichloromethane. The organic layers were combined and washed with water, dried over sodium sulfate and concentrated. Yield: 9.95 g. TLC: Rf=0.31, heptane/ethyl acetate 1/1.

Cbz-D-Tyr(tBu)OMe

[2-(1H-benzotriazol-1-yl)-1,1,3,3-tetramethyluronium tetrafluoroborate] (7.45 g) was added to a solution of Cbz-D-Tyr(tBu)-OH (9.95 g) in dichloromethane (45) and methanol (5 ml). The pH of the mixture was adjusted to 8 with N,N-diisopropylethylamine. The reaction mixture was stirrred for 1 hour at room temperature and then quenched with 5% sodium hydrogencarbonate. The organic phase was separated and washed with water, 2% citric acid and brine, dried over sodium sulfate and concentrated under reduced pressure. Yield: 10.2 g.

TLC:Rf=0.74, heptane/ethyl acetate 1/1.

H—D-Tyr(tBu)-OMe.HCl

10% palladium on charcoal (1.2 g) was added to a solution of Cbz-D-Tyr(tBu)-OMe (10.2 g) in methanol (100 ml) and 4N hydrogen chloride (5 ml). The mixture was hydrogenated at atmospheric pressure at room temperature for 2 hours. The palladium catalyst was removed by filtration. The filtrate was concentrated to a small volume followed by cystallisation from diethyl ether. Yield: 5.87 g. TLC: Rf=0.10, heptane/ethyl acetate 1/1.

HOOC—$CH_2$—D-Tyr-Pro-Lys-(2-thiazolyl)

This compound was prepared in a similar manner as described in example 24, starting from H—D-Tyr(tBu)-OMe.HCl. Deprotection of 586 mg N-(t-butyloxycarbonylmethyl)-N-Boc-D-Tyr(tBu)-Pro-Lys(Cbz)-(2-thiazolyl), according to the procedures described in example 1, gave 283 mg of the product, after HPLC purification.

$R_t$ (LC)=20.9 min, 20% A, 80% B to 20% A, 20% B and 60% C in 40 min.

EXAMPLE 33

HOOC—$CH_2$—D/L-p-$CH_3$-Phe-Pro-Lys-(2-thiazolyl)

H—D/L-p-$CH_3$-Phe-OH.HCl

A suspension of sodium hydride (3.28 g, 60% dispersion in mineral oil) in ethanol (40 ml) was added to a solution of a-chloro-p-xylene (10 g), diethyl acetamidomalonate (19.3 g) and sodium iodide (8.55 g) in dioxane (80 ml) and ethanol (20 ml). The reaction mixture was refluxed at 80° C. for 90 min. The solvent was removed under reduced pressure and the residue was dissolved in ethyl acetate. The organic phase was washed with 5% sodium hydrogensulfate, 5% sodium hydrogensulfite, water, 5% sodium hydrogencarbonate and brine, dried over sodium sulfate and concentrated in vacuo. The product was crystallised from heptane to afford 19.8 g of the condensation product. This was treated with 6 N hydrogen chloride (420 ml) and acetic acid (210 ml) overnight at 95° C. to afford, after evaporation to dryness, 21.6 g of the product.

TLC: Rf=0.15, silca gel, ethyl acetate/pyridine/acetic acid/water 664/31/18/7 v/v/v/v .

HOOC—$CH_2$—D/L-p-$CH_3$-Phe-Pro-Lys-(2-thiazolyl)

According to the same methods as described in example 24, HOOC—$CH_2$—D/L-p-$CH_3$-Phe-Pro-Lys-(2-thiazolyl) was prepared starting from H—D/L-p-$CH_3$-Phe-OH.HCl. Removal of the blocking groups from the protected tripeptide (582 mg) and HPLC purification was performed under similar conditions as described in example 1. Yield: 120 mg.

$R_t$ (LC)=31.9 min, 20% A, 80% B to 20% A, 20% B and 60% C in 40 min.

EXAMPLE 34

HOOC—$CH_2$—D-m-Cl-Phe-Pro-Lys-(2-thiazolyl)

Starting from 3-chloro benzylbromide, H—D/L-m-Cl-Phe-OH.HCl was prepared as described in example 33. Next, the fully protected tripeptide was assembled according to the same procedures as described in example 26. In the final step 1 g N-(t-butyloxycarbonylmethyl)-N-Boc-D/L-m-Cl-Phe-Pro-Lys(Cbz)-(2-thiazolyl) was treated with trifluoroacetic acid and thioanisole (see example 1). After HPLC purification 195 mg HOOC—$CH_2$—D-m-Cl-Phe-Pro-Lys-(2-thiazolyl) was isolated.

$R_t$ (LC)=31.7 min, 20% A, 80% B to 20% A, 20% B and 60% C in 40 min.

EXAMPLE 35

HOOC—$CH_2$—D-DPA-Pro-Lys-(2-thiazolyl). (DPA=diphenylalanine)

This compound was prepared in a similar manner as described in example 24, starting from H—D-DPA-OH.HCl. Deprotection of 570 mg N-(t-butyloxycarbonylmethyl)-N-Boc-D-DPA-Pro-Lys(Cbz)-(2-thiazolyl), according to the methods described in example 1, afforded after HPLC purification 194 mg end product.

$R_t$ (LC)=35.6 min, 20% A, 80% B to 20% A, 20% B and 60% C in 40 min.

EXAMPLE 36

HOOC—$CH_2$—D-m-OH-Phe-Pro-Lys-(2-thiazolyl)

This compound was prepared in a similar manner as described in example 24, starting from H—D/L-m-OH-Phe-OH.HCl. The phenolic hydroxyl function was also protected with a Boc group during the introduction of the Boc group on the N-terminus. Deprotection (see example 1) of 1.21 g N-(t-butyloxycarbonylmethyl)-N-Boc-D/L-m-Boc-Phe-Pro-Lys(Cbz)-2-thiazolyl) afforded after HPLC purification the desired diastereoisomer. Yield: 99 mg.

$R_t$ (LC)=23.8 min, 20% A, 80% B to 20% A, 20% B and 60% C in 40 min.

EXAMPLE 37

HOOC—$Ch_2$—D/L-m-$OCH_3$-Phe-Pro-Lys-(2-thiazolyl)

Boc-D/L-mOH-Phe-OH

H—D/L-m-OH-Phe-OH.HCl (5.25 g) was dissolved in dioxane (55 ml), water (28 ml) and 1 N sodium hydroxide solution (29.0 ml). Di-t-butyl dicarbonate (6.95 g) was added and the reaction mixture was stirred overnight at room temperature at pH 9. The reaction mixture was diluted with water (200 ml) and extracted with heptane. The aqueous layer was diluted with ethyl acetate (150 ml) and acidified to pH 2 with 1N hydrogen chloride. The organic phase was separated and the water layer was extracted with ethyl acetate. The organic layers were combined and washed with water and brine, dried over sodium sulfate and concentrated in vacuo. Yield: 8.49 g.

TLC: $R_f$=0.67, silica gel, ethyl acetate/pyridine/acetic acid/water 126/20/6/11 v/v/v/v.

Boc-D/L-m-OCH$_3$-Phe-OMe

A mixture of Boc-D/L-m-OH-Phe-OH (8.49 g), sodium carbonate (23.9 g) and iodomethane (20.3 ml) in N,N-dimethyl formamide (60 ml) was stirred at 60° C. for 48 h. Next, the reaction mixture was poured into ice-water and acidified to pH 2.5 with 2 N hydrogen chloride, followed by extraction with ethyl acetate. The organic layers were combined and washed with water and brine, dried over sodium sulfate and concentrated in vacuo. The crude product was purified by silica gel chromatography using heptane/ethyl acetate 7/3 v/v. Yield: 6.66 g.

TLC: $R_f$=0.56, silica gel, heptane/ethyl acetate 3/2 v/v.

H—D/L-m-OCa-Phe-OMe.TFA

Boc-D/L-m-OCH$_3$-Phe-OMe (6.66 g) was dissolved in dichloromethane (20 ml) and trifluouroacetic acid (20 ml) and stirred at room temperature for 2 hours. The solvent was removed under reduced pressure and the crude product was coevaporated from toluene twice. Yield: 9.56 g.

TLC: $R_f$=0.32, silica gel, ethyl acetate/pyridine/acetic acid/water 126/20/6/11 v/v/v/v.

HOOC—CH$_2$—D/L-m-OCH$_3$-Phe-Pro-Lys-(2-thiazolyl)

H—D/L-m-OCH$_3$-Phe-OMe.TFA was used to assemble N-(t-butyloxycarbonylmethyl)-N-Boc-D/L-m-OCH$_3$-Phe-Pro-Lys(Cbz)-(2-thiazolyl) according to the same route as described in example 24, Treatment of 624 mg of the protected tripeptide with trifluoroacetic acid and thioanisole (see example 1), followed by HPLC purification afforded 114 mg of the product.

$R_t$ (LC)=29.3 min and 29.8 min, 20% A, 80% B to 20% A, 20% B and 60% C in 40 min.

EXAMPLE 38

HOOC—CH$_2$—D/L-p-Br-Phe-Pro-Lys-(2-thiazolyl)

Boc-D/L-p-Br-Phe-OH

A suspension of H—D/L-p-Br-Phe-OH (2.44 g) in 25 ml t-butanol/water 1/1 v/v was adjusted to pH 9 with sufficient diluted sodium hydroxide (1 N) solution. Di-t-butyl dicarbonate (3.27 g) was added and the reaction mixture was stirred overnight while the pH was kept at 9. The reaction mixture was diluted with water, followed by extraction with heptane. The water layer was diluted with ethyl acetate and subsequently acidified to pH 2.5 using 2 N hydrogen chloride. The organic phase was separated and the aqueous phase was extracted with ethyl acetate. The organic layers were combined and washed with water and brine, dried over sodium sulfate and concentrated in vacuo. Yield: 3.35 g.

TLC: $R_f$=0.32, silica gel, ethyl acetate/pyridine/acetic acid/water 126/20/6/11 v/v/v/v.

Boc-D/L-p-Br-Phe-Pro-OH

Boc-D/L-pBr-Phe-OH (3.35 g) was coupled with H-Pro-OMe.HCl and subsequently saponified with sodium hydroxide according to the same methods as described in example 26. Yield: 3.13 g. TLC: Rf=0.45, silica gel, ethyl acetate/methanol 9/1.

Boc-D/L-p-Br-Phe-Pro-Lys(Cbz)-(2-thiazolyl)

Coupling of Boc-D/L-p-Br-Phe-Pro-OH (750 mg) with H-Lys(Cbz)-(2-thiazolyl) was performed under the same conditions as described in example 24. Yield: 1.01 g.

TLC: $R_f$=0.85, silica gel, dichloromethane/methanol 9/1 v/v.

H—D/L-p-Br-Phe Pr L s(Cbz42-thiazolyl.TFA

Boc-D/L-p-Br-Phe-Pro-Lys(Cbz)2-thiazolyl) (1.01 g) was dissolved in trifluoroacetic acid (TFA, 10 ml) and stirred for 1 hour at room temperature. The solvent was removed under reduced pressure. Yield: 879 mg.

TLC: $R_f$=0.75 and 0.68, silica gel, ethyl acetate/pyridine/acetic acid/water 63/20/6/11 v/v/v/v.

N-(t-butyloxycarbonylmethyl)-D/L-p-Br-Phe-Pro-Lys(Cbz)-(2-thiazolyl)

t-Butyl bromoacetate (264 ml) was added to a solution of H—D/L-p-Br-Phe-Pro-Lys(Cbz)-(2-thiazolyl).TFA (879 mg) in acetonitrile (25 ml). The pH of the reaction mixture was adjusted to 8 with N,N-diisopropylethylamine whereafter the reaction mixture was allowed to stand overnight at room temperature. The solvent was removed by evaporation and the residue was dissolved in ethyl acetate. The organic phase was washed with water, 5% sodium hydrogencarbonate and brine, dried over sodium sulfate and concentrated in vacuo. The crude product was purified over silica gel using dichloromethane/methanol 95/5 v/v to afford 850 mg of the protected tripeptide.

TLC: $R_f$=0.91, silica gel, ethyl acetate/pyridine/acetic acid/water 63/20/6/11 v/v/v/v.

HOOC—CH$_2$—D/L-p-Br-Phe-Pro-Lys-(2-thiazolyl)

N-(t-butyloxycarbonylmethyl)-D/L-p-Br-Phe-Pro-Lys(Cbz)-(2-thiazolyl) (850 mg) was treated under the same conditions with trifloroacetic acid and thioanisole as described in example 1 to obtain, after HPLC purification, 123 mg of the product.

$R_t$ (LC)=33.9 min and 34.4 min, 20% A, 80% B to 20% A, 20% B and 60% C in 40 min.

EXAMPLE 39

HOOC—CH$_2$—D-p-F-Phe-Pro-Lys-(2-thiazolyl)

This compound was prepared in a similar manner as described in example 38, starting from H—D-p-F-Phe-OH. Deprotection (see example 1) of 563 mg N-(t-butyloxycarbonylmethyl)-D-p-F-Phe-Pro-Lys(Cbz)-(2-thiazolyl) gave, after HPLC purification, 182 mg of the product.

$R_t$ (LC)=29.7 min, 20% A, 80% B to 20% A, 20% B and 60% C in 40 min.

EXAMPLE 40

HOOC—CH$_2$—D/L-m,p-di-Cl-Phe-Pro-Lys-(2-thiazolyl)

This compound was prepared in a similar manner as described in example 38, starting from H—D/L-m,p-di-Cl- Phe-OH. Deprotection (see example 1) of 480 mg N-(t-butyloxycarbonylmethyl)-D/L-m,p-di-Cl-Phe-Pro-Lys(Cbz) 2-thiazolyl) gave, after HPLC purification, 191 mg of the product.

$R_t$ (LC)=36.8 min and 37.8 min, 20% A, 8/B to 20% A, 20% B and 60% C in 40 min.

EXAMPLE 41

BzlSO$_2$-norLeu(cyclo)Gly-LysΨ[COCO]—OH (Bzl=benzyl)

Cbz-Lys(Boc)-OMe

Cbz-Lys(Boc)-OH (28 g) was dissolved in dichloromethane/methanol=9/1 v/v (500 ml). 2-(1H-benzotriazol-1-yl)-1,1,3,3-tetramethyluronium tetrafluoroborate (23.6 g) was added and the solution adjusted to pH 8 by addition of triethylamine. The reaction mixture was stirred for 2 h at room temperature. The mixture was washed successively with cold 1N hydrogen chloride solution, water, 5% sodium hydrogencarbonate, and water and dried over sodium sulfate. The filtrate was evaporated and the residue was chromatographed on silica gel in ethyl acetate/heptane=1/4 v/v as eluent. The fractions containing Cbz-Lys(Boc)-OMe were pooled and evaporated. Yield: 29.1 g TLC: $R_f$=0.85, silica gel, ethyl acetate/heptane=3/1 v/v.

Cbz-Lys(Boc)Ψ[cyanoacetate]

To a cold (−78° C.) solution of Cbz-Lys(Boc)-OMe (29.1 g) in dry dichloromethane (800 ml) was added dropwise diisobutyl aluminumhydride (222 ml of 1M solution in hexane) at a rate to keep the reaction temperature below −70° C. The resulting solution was stirred at −78° C. for 1 h. A 5% citric-acid solution (600 ml) was added to the reaction mixture. The two layer mixture was stirred at room temperature for 10 minutes, the layers were separated and the aqueous layer was extracted with dichloromethane. The combined dichloromethane layers were washed with water and dried over sodium sulfate and filtered. The solution was placed under nitrogen and cooled on a icewater-bath. A solution of sodium cyanide (36.3 g) and benzyltriethyl ammonium chloride (4.2 g) in water (600 ml) was added. Under vigorous stirring acetic anhydride was added portionwise (2×9 ml) over a period of 30 min. The organic layer was separated and the aqueous layer was extracted with dichloromethane. The combined dichloromethane layers were washed with water, dried over sodium sulfate, filtered and evaporated in vacuo. The residue was purified by chromatography on silica (eluent heptane/ethyl acetate=1/1 v/v) to yield Cbz-Lys (Boc)Ψ[cyanoacetate] (26.3 g.) .

TLC: Rf=0.60, silica gel, dichloromethane/ethyl acetate=7/3 v/V.

Cbz-Lys(Boc)Ψ[CHOHCO]—OMe

A solution of Cbz-Lys(Boc)Ψ[cyanoacetate] (26.3 g.) in diethyl ether/methanol=3/1 v/v (600 ml) was cooled to −20° C. under nitrogen, and 66 g of gaseous hydrochloric acid was introduced keeping the temperature below −5° C. The reaction mixture was kept at 4° C. overnight. Water (100 ml) was added dropwise to the reaction mixture keeping the temperature below 5° C. After stirring for 16 h at room temperature the organic layer was separated and washed with water. The aqueous layer was saturated with sodium chloride and extracted with sec-butanoldichloromethane=3/2 v/v. The organic phase was washed with brine, dried over sodium sulfate, filtered and evaporated in vacuo to give 25.4 g of the crude amine. The residue was taken up in N,N-dimethyl formamide (400 ml), and bis-(tert-butyl)anhydride (16 g) was added and triethylamine until pH 8. The reaction mixture was stirred at room temperature overnight. The solvent was removed by evaporation at reduced pressure. The residue was dissolved in ethyl acetate, washed with water and brine successively, dried over sodium sulfate, filtered and evaporated in vacuo. The residue was purified by chromatography on silica (eluent:

ethyl acetate/heptane=4/6 v/v) to yield Cbz-Lys(Boc)Ψ[CHOHCO]—OMe (15.8 g).

TLC: Rf=0.75, silica gel, ethyl acetate/pyridine/acetic acid/water=63/20/6/11 v/v/v/v.

H-Lys(Boc)Ψ[CHOHCO]—OMe

10% palladium on charcoal (92 mg) and 2.18 ml of a 1N hydrochloride solution were added to a solution of Cbz-Lys (Boc)Ψ[CHOHCO]—OMe (0.92 g) in N,N-Dimethyl formamide (20 ml). The mixture was hydrogenated at atmospheric pressure at room temperature for 3 h. The palladium catalyst was removed by filtration and the solvent was removed by evaporation at reduced pressure yielding H-Lys(Boc)Ψ[CHOHCO]—OMe.HCl quantitatively.

TLC: $R_f$=0.47, silica gel, ethyl acetate/pyridine/acetic acid/water=88/31/18/7 v/v/v/v.

BzlSO$_2$-norLeu(cyclo)Gly-Lys(Boc)Ψ [CHOHCO]—OMe (S)-3-benzylsylfonylamido-2-oxo-1-azepineacetic acid was prepared according to the procedure in example 18. To a cold (0° C.) solution of (S)-3-benzylsulfonylamido-2-oxo-1-azepineacetic acid (BzlSO$_2$-norLeu(cyclo)Gly) (400 mg) in N,N-dimethyl formamide (20 ml) were successively added 1-hydroxy benzotriazole (238 mg), dicyclohexyl carbodiimide (267 mg), H-Lys(Boc)Ψ[CHOHCO]—OMe.HCl (385 mg) and triethylamine (0.32 ml). The mixture was stirred at 0° C. for 1 hour and then kept at room temperature overnight. The mixture was cooled to −20° C. and dicyclohexylurea was removed by filtration. The filtrate was evaporated to dryness. The residue was dissolved in ethyl acetate and washed successively with 5% sodium hydrogen carbonate, water, 2% citric acid, saturated aqueous sodium chloride, dried over sodium sulfate and concentrated in vacuo. The residue was chromatographed on silica gel in dichloromethane/methanol=9/1 (v/v) as eluent. The fractions containing BzlSO$_2$-norLeu(cyclo)Gly-Lys(Boc)Ψ[CHOHCO]—OMe were pooled and evaporated. Yield: 663 mg.

TLC: $R_f$=0.91, silica gel, ethyl acetate/pyridine/acetic acid/water=63/20/6/11 v/v/v/v.

BzlSO$_2$-norLeu(cyclo)Gly-Lys(Boc)Ψ [CHOHCO]—OH

BzlSO$_2$-norLeu(cyclo)Gly-Lys(Boc)Ψ[CHOHCO]—OMe (650 mg) was dissolved in dioxane/water-7/3 v/v (20 ml) and treated with 2M sodium hydroxide solution (1.05 ml) portionwise over 1 h at room temperature, keeping the pH at 12–13. The reaction mire was diluted with water (20 ml), 2M hydrogen chloride solution was added until pH 2.0 and the water layer was extracted with dichloromethane. The combined organic phases were washed with water, brine and dried over sodium sulfate, filtered and concentrated in vacuo to yield BzlSO$_2$-norLeu(cyclo)Gly-Lys(Boc)Ψ[CHOHCO]—OH (740 mg).

TLC: $R_f$=0.44, silica gel, ethyl acetate/pyridine/acetic acid/water=63/20/6/11 v/v/v/v.

BzlSO$_2$-norLeu(cyclo)Gly-Lys(Boc)Ψ[COCO]—OH

To a solution of BnSO$_2$-norLeu(cyclo)Gly-Lys(Boc)Ψ[CHOHCO]—OH (740 mg) in dry dichloromethane (20 ml) was added 450 mg of periodinane (Dess-Martin reagent). After 1 h stirring at room temperature, 2% sodium thiosulfate solution was added (20 ml) and the mixture was stirred for 30 min at room temperature. The organic layer was separated, washed with water, dried over sodium sulfate, filtered and evaporated in vacuo to give crude BzlSO$_2$-norLeu(cyclo)Gly-Lys(Boc)Ψ[COCO]—OH (497 mg).

TLC: R$_f$=0.45, silica gel, ethyl acetate/pyridine/acetic acid/water=63/20/6/11 v/v/v/v.

BzlSO$_2$-norLeu(cyclo)Gly-LysΨ[COCO]—OH

BzlSO$_2$-norLeu(cyclo)Gly-Lys(Boc)Ψ[COCO]—OH (497 mg, crude) was treated with 90% trifluoroacetic acid/water (10 ml) for 1 h at room temperature. The reaction mixture was concentrated in vacuo and the residue dissolved in water and directly charged onto a preparative HPLC DeltaPak RP-C$_{18}$ using a gradient elution system of 20% A/80% B to 20% A/45% B/35% C over 45 min at a flow rate of 80 ml/min. Yield: 200 mg of BzlSO$_2$-norLeu(cyclo)Gly-LysΨ[COCO]—OH.

R$_t$ (LC): 26.37 min; 20% A/80% B to 20% A/20% B/60% C in 40 min.

EXAMPLE 42

H—(—CH$_3$)—D-norLeu-Pro-LysΨ[COCO]—OH

Boc-(N—CH$_3$)-NorLeu-Pro-OH

This compound was prepared according to example 11. In a similar manner as described in example 1 was prepared: H—(N—CH$_3$)—D-NorLeu-Pro-LysΨ[COCO]—OH Yield: 69 mg R$_t$ (LC): 13.27 min; 20% A/80% B to 20% A/20% B/60% C in 40 min.

EXAMPLE 43

H—D-Phe-Pro-LysΨ[COCO]—OH

Boc-D-Phe-Pro-OMe

To a cold (0° C.) solution of Boc-D-Phe-OH (5 g) in N,N-dimethyl formamide (200 ml) were successively added 1-hydroxy benzotriazole (4.29 g), dicyclohexyl carbodimide (4.29 g), H-Pro-OMe.HCl (3.1 g) and N-ethylmorpholine (3 ml). The mixture was stirred at 0° C. for 1 hour and then kept at room temperature for 2 days. The mixture was cooled to −20° C. and dicyclohexylurea was removed by filtration. The filtrate was evaporated to dryness. The residue was dissolved in ethyl acetate and washed successively with 5% sodium hydrogen carbonate, 0.1M hydrogen chloride-solution, saturated aqueous sodium chloride, dried over sodium sulfate and concentrated in vacuo. The residue was chromatographed on silica gel in heptane/ethyl acetate=6/4 (v/v) as eluent. The fractions containing Boc-D-Phe-Pro-OMe were pooled and evaporated. Yield: 1.5 g.

TLC: R$_f$=0.90, silica gel, ethyl acetate/pyridine/acetic acid/water-163/20/6/11 v/v/v/v.

Boc-D-Phe-Pro-OH

Boc-D-Phe-Pro-OMe (8.3 g) was dissolved in dioxane/water=6/4 v/v (150 ml) and treated with 2M sodium hydroxide solution (16.5 ml) portionwise over 1 h at room temperature, keeping the pH at 12.5. 2M hydrogen chloride solution was added to the reaction mixture until pH 3.0 and the water layer was extracted with ethyl acetate. The combined organic phases were washed with water, brine and dried over sodium sulfate, filtered and concentrated in vacuo to yield Boc-D-Phe-Pro-OH (6.9 g).

TLC: R$_f$=0.30, silica gel, ethyl acetate/pyridine/acetic acid/water=213/20/6/11 v/v/v/v.

In a similar manner as described in example 1 was prepared: H—D-Phe-Pro-LysΨ[COCO]—OH. Yield: 417 mg R$_t$ (LC): 16.22 min; 20% A/80%o B to 20% A/20% B/60% C in 40 min.

EXAMPLE 44

H—(N—CH$_3$)—D-Phe-(N-cyclopentyl)-Gly-LysΨ[COCO]—OH

Boc-(N—CH$_3$)—D-Phe-(N-cyclopentyl)-Gly-OH

This compound was prepared as described in example 3 using Boc-(N—CH$_3$)—D-Phe-OH and HCl.H-(N-cyclopentyl)-Gly-OMe.

TLC: R$_f$=0.52, silica gel, dichloromethane/methanol=9/1 v/v.

In a similar manner as described in example 1 was prepared:
H—(N—CH$_3$)—D-Phe-(N-cyclopentyl)-Gly-LysΨ[COCO]—OH. Yield: 87 mg R$_t$ (LC): 23.92 min; 20% A/80% B to 20% A/20% B/60% C in 40 min.

EXAMPLE 45

Ethylsulfonyl-D-Phe-Pro-LysΨ[COCO]—OH

Ethylsulfonyl-D-Phe-Pro-OH

This compound was prepared according to example 22.

In a similar manner as described in example 41 was prepared:
Ethylsulfonyl-D-Phe-Pro-LysΨ[COCO]—OH. Yield: 90 mg.

R$_t$ (LC) 28.04 min; 20% A/80% B to 20% A/20% B/60% C in 40 mnm.

EXAMPLE 46

(4aR,8aR)-perhydroisoquinoline-1(R)-carbonyl-Pro-LysΨ[COCO]—OH

2-Cbz-(4aR,8aR)-perhydroisoquinoline-1(R)-carbonyl-Pro-OH

This compound was prepared according to example 20.

In a similar manner as described in example 41 was prepared:
(4aR,8aR)-perhydroisoquinoline-1(R)-carbonyl-Pro-LysΨ[COCO]—OH. Yield: 170 mg.

R$_t$ (LC): 18.95 min; 20% A/80% B to 20% A/20% B/60% C in 40 min.

EXAMPLE 47

HOOC—CH$_2$—D-Coa-Pro-Lys-(2-thiazolyl) (Coa=cyclo-octylalanine)

Cyclo-octylmethyl Bromide

Cyclooctylmethanol (8.16 g) was dissolved in 47% HBr-solution (70 ml) and refluxed for 1 hour at 130° C. The reaction mixture was poured onto icewater (500 ml) and saturated sodium hydrogencarbonate solution (500 ml) was added. The aqueous solution was extracted with dichloromethane. The combined organic phases were washed with water, brine and dried over sodium sulfate, filtered and concentrated in vacuo. The residue was chromatographed on silica gel in toluene as eluent. The fractions containing cyclo-octylmethyl bromide were pooled and evaporated. Yield: 9.85 g. TLC: $R_f$=0.95, silica gel, toluene (R,S)-Ethyl-2acetylamino-2-cyano-3-cyclooctyl-propionate Potassium tert.-butylate (6.85 g) and ethyl acetamidocyanoacetate (8.1 g) were dissolved in dimethylsulfoxide (100 ml) at room temperature. Cycol-octylmethyl bromide was dissolved in dimethylsulfoxide (25 ml) and added dropwise to the reaction mixture. The mixture was stirred at room temperature for 44 hours. After pouring onto 500 ml water the precipitate was filtered and dried to yield (R,S)-ethyl-2-acetylamino-2-cyano-3-cyclooctyl-propionate (2.95 g)

TLC: $R_f$=0.50, silica gel, heptane/ethyl acetate=3/7 v/v.

H—D,L—Cyclo-octylalanine-OH.HCl (R,S)ethyl-2-acetylamino-2-cyano-3-cyclooctyl-propionate (2.95 g) was suspended in 100 ml of a 20%/hydrogen chloride-solution and refluxed for 22 hours. The reaction mixture was cooled to 5° C. and the precipitate formed was filtered, washed with diethyl ether and dried.

Yield: 2.69 g H-D,L-Cyclo-octylalanine-OH.HCl (H—D,L—Coa-OH.HCl)

TLC: $R_f$=0.27, silica gel, ethyl acetate/pyridine/acetic acid/water=63/20/6/11 v/v/v/v.

In a similar manner as described in example 24 was prepared: HOOC—CH$_2$—D-Coa-Pro-Lys-(2-thiazolyl). Yield: 162 mg.

$R_t$ (LC): 38.35 min; 20% A/80% B to 20% A/20% B/60% C in 40 min.

In a similar manner as described in example 24 were prepared:

EXAMPLE 48

HOOC—CH$_2$—D-2-Nal-Pro-Lys-(2-thiazolyl) (Nal=naphthylalanine)

Yield: 423 mg $R_t$ (LC): 35.78 min; 20% A/80% B to 20% A/20% B/60% C in 40 min

EXAMPLE 49

HOOC—CH$_2$—D-norLeu-Pro-Lys-(2-thiazolyl)

Yield: 344 mg $R_t$ (LC): 24.84 min; 20% A/80% B to 20% A/20% B/60% C in 40 min

EXAMPLE 50

HOOC—CH$_2$—D-Leu-Pro-Lys-(2-thiazolyl)

Yield: 138 mg $R_t$ (LC): 24.50 min; 20% A/80% B to 20% A/20% B/60% C in 40 min

EXAMPLE 51

Anti-thrombin Assay

Thrombin (Factor IIa) is a factor in the coagulation cascade.

The anti-thrombin activity of compounds of the present invention was assessed by measuring spectrophotometrically the rate of hydrolysis of the chromogenic substrate s-2238 exterted by thrombin. This assay for anti-thrombin activity in a buffer system was used to assess the $IC_{50}$-value of a test compound.

Test medium: Tromethamine-NaCl-polyethylene glycol 6000 (TNP) buffer. Reference compound: I2581 (Kabi) Vehicle:TNP buffer. Solubilisation can be assisted with dimethylsulphoxide, methanol, ethanol, acetonitrile or tert.-butyl alcohol which are without adverse effects in concentrations up to 2.5% in the final reaction mixture.

Technique Reagents*: 1. Tromethamine-NaCl (TN) buffer. Composition of the buffer: Tromethamine(Tris) 6.057 g (50 mmol), NaCl 5.844 g (100 mmol), water to 1 l. The pH of the solution is adjusted to 7.4 at 37° C. with HCl (10 mmol·l$^{-1}$). 2. TNP buffer: Polyethylene glycol 6000 is dissolved in TN buffer to give a concentration of 3 g·l$^{-1}$. 3. S-2238 solution: One vial S-2238 (25 mg; Kabi Diagnostica, Sweden) is dissolved in 20 ml TN buffer to give a concentration of 1.25 mg·ml$^{-1}$ (2 mmol·l$^{-1}$). 4. Thrombin solution: Human thrombin (16 000 nKat·vial$^{-1}$; Centraal Laboratorium voor Bloedtransfusie, Amsterdam, The Netherlands) is dissolved in TNP buffer to give a stock solution of 835 nKat·ml$^{-1}$. Immediately before use this solution is diluted with TNP buffer to give a concentration of 3.34 nKat·ml$^{-1}$.

* All ingredients used are of analytical grade

For aqueous solutions ultrapure water (Milli-Q quality) is used.

Preparation of Test and Reference Compound Solutions

The test and reference compounds are dissolved in Milli-Q water to give stock concentrations of $10^{-2}$ mol·l$^{-1}$. Each concentration is stepwise diluted with the vehicle to give concentrations of $10^{-3}$, $10^{-4}$ and $10^{-5}$ mol·l$^{-1}$. The dilutions, including the stock solution, are used in the assay (final concentrations in the reaction mixture: $3·10^{-3}$; $10^{-3}$; $3·10^{-4}$; $10^{-4}$; $3·10^{-5}$; $10^{-5}$; $3·10^{-6}$ and $10^{-6}$ mol·l$^{-1}$, respectively).

Procedure

At room temperature 0.075 ml and 0.025 ml test compound or reference compound solutions or vehicle are alternately pipetted into the wells of a microtiter plate and these solutions are diluted with 0.115 ml and 0.0165 ml TNP buffer, respectively. An aliquot of 0.030 ml S-2238 solution is added to each well and the plate is pre-heated and pre-incubated with shaking in an incubator (Amersham) for 10 min. at 37° C. Following pre-incubation the hydrolysis of S-2238 is started by addition of 0.030 ml thrombin solution to each well. The plate is incubated (with shaking for 30 s) at 37° C. Starting after 1 min of incubation, the absorbance of each sample at 405 nm is measured every 2 min. for a period of 90 min. using a kinetic microtiter plate reader (Twinreader plus, Flow Laboratories).

All data are collected in an IBM personal computer using LOTUS-MEASURE. For each compound concentration (expressed in mol·l$^{-1}$ reaction mixture) and for the blank the absorbance is plotted versus the reaction time in min.

Evaluation of responses: For each final concentration the maximum absorbance was calculated from the assay plot. The $IC_{50}$-value (final concentration, expressed in ‖mol·l$^{-1}$, causing 50% inhibition of the maximum absorbance of the blank) was calculated using the logit transformation analysis according to Hafner et al. (Arzneim.-Forsch./Drug Res. 1977; 27(II): 1871–3).

In the following table, $IC_{50}$-values of compounds of the invention are listed:

| Example | IC$_{50}$-value ($\mu$M) |
|---------|--------------------------|
| 2(e)    | 4.5                      |
| 4(b)    | 4.34                     |
| 39      | 19                       |
| 41      | 0.135                    |

We claim:

1. A non-slow-binding thrombin inhibitor of the formula:

A—B—C-Lys-D wherein

A is —CO—(CH$_2$)$_n$COOH or —(CHR$_2$)$_n$COOH, wherein n is 1 or 2 and R$_2$ is H or methyl;

B is selected from D-Cha, D-Coa, norLeu, Leu, Nal, DPA, Tyr and D-Phe optionally mono- or di-substituted with methoxy or halogen:

C is Pro, or —N(cyclopentyl)-CH$_2$—CO—;

D is thiazolyl or oxazolyl;

or a prodrug thereof;

or a pharmaceutically acceptable salt thereof.

2. The non-slow-binding thrombin inhibitor of claim 1, wherein D is thiazolyl.

3. A compound of the formula: HOOC—CH$_2$—D-Cha-Pro-Lys-(2-thiazolyl).

4. A pharmaceutical composition comprising the non-slow-binding thrombin inhibitor of claim 1 or 2 and a pharmaceutically acceptable auxiliary.

5. A pharmaceutical composition comprising the compound of claim 3 and a pharmaceutically acceptable auxiliary.

6. A process for preparing a non-slow-binding thrombin inhibitor of claim 1, 2 or 3, comprising coupling suitably protected amino acids or amino acid analogs, followed by removing the protecting groups.

7. A method for treating conditions involving undesired blood coagulation in a patient, comprising administering a thrombin-inhibiting effective amount of a non-slow-binding thrombin inhibitor of any one of claim 1, 2 or 3 to said patient.

8. A process for making a pharmaceutical composition, comprising admixing a non-slow-binding thrombin inhibitor of any one of claims 1, 2 or 3 with pharmaceutically acceptable auxiliaries.

* * * * *